(12) United States Patent
Ferree

(10) Patent No.: US 6,802,844 B2
(45) Date of Patent: Oct. 12, 2004

(54) SPINAL ALIGNMENT APPARATUS AND METHODS

(75) Inventor: Bret A. Ferree, Cincinnati, OH (US)

(73) Assignee: NuVasive, Inc, San Diego, CA (US)

( * ) Notice: Subject to any disclaimer, the term of this patent is extended or adjusted under 35 U.S.C. 154(b) by 69 days.

(21) Appl. No.: 10/105,971

(22) Filed: Mar. 25, 2002

(65) Prior Publication Data

US 2002/0138077 A1 Sep. 26, 2002

Related U.S. Application Data

(60) Provisional application No. 60/278,910, filed on Mar. 26, 2001.

(51) Int. Cl.[7] .............................................. A61B 17/56
(52) U.S. Cl. .......................................... 606/61; 606/60
(58) Field of Search .............................. 606/61, 69, 70, 606/71, 72, 73, 74, 75, 104, 105

(56) References Cited

U.S. PATENT DOCUMENTS

| | | |
|---|---|---|
| 4,361,141 A | 11/1982 | Tanner |
| 4,771,767 A | 9/1988 | Steffee |
| 4,805,602 A | 2/1989 | Puno et al. ................... 128/69 |
| 4,946,458 A | 8/1990 | Harms et al. ................. 606/61 |
| 4,998,936 A | 3/1991 | Mehdian ...................... 606/61 |
| 5,042,982 A | 8/1991 | Harms et al. ................. 606/61 |
| 5,084,049 A | 1/1992 | Asher et al. .................. 606/61 |
| 5,092,866 A | 3/1992 | Graf et al. |
| 5,092,867 A | 3/1992 | Harms et al. ................. 606/61 |
| 5,129,388 A | 7/1992 | Lapreste et al. |
| 5,176,680 A | 1/1993 | Vignaud et al. .............. 606/61 |
| 5,196,013 A | 3/1993 | Harms et al. ................. 606/61 |
| 5,207,678 A | 5/1993 | Harms et al. ................. 606/61 |
| 5,261,907 A | 11/1993 | Vignaud et al. .............. 606/60 |
| 5,275,600 A | 1/1994 | Allard et al. ................. 606/61 |

(List continued on next page.)

FOREIGN PATENT DOCUMENTS

| | | |
|---|---|---|
| DE | 3722590 C1 | 12/1988 |
| DE | 3841008 A1 | 6/1990 |
| EP | 0 128 058 A1 | 12/1984 |
| EP | 0 283 373 A1 | 9/1988 |
| EP | 0 348 272 A1 | 12/1989 |
| EP | 1 072 228 A1 | 1/2001 |
| FR | 82 09023 | 12/1982 |
| FR | 2 559 378 A1 | 4/1985 |
| FR | 2 624 720 A1 | 6/1989 |
| GB | 2 780652 | 8/1957 |

OTHER PUBLICATIONS

Ebrahim, "Posterior Lateral Mass Screw Fixation . . . ", U.P.O.J., vol. 12, Spring 1999, pp. 66–72.

(List continued on next page.)

*Primary Examiner*—Cary E. O'Connor
*Assistant Examiner*—Candice C. Melson
(74) *Attorney, Agent, or Firm*—Jonathan Spangler

(57) ABSTRACT

Spinal alignment apparatus includes bodies which connect to vertebra to be aligned, and elongated elements that connect to the bodies. The elements are adjustable relative to the bodies in multiple dimensions, with locking mechanisms that allow the alignment to proceed in an orderly fashion until a desired degree of correction is achieved. Each elongated element has a shaped end terminating in the first portion of the lockable coupling mechanism. The vertebral connector bodies each include a feature for attaching the body to a respective vertebrae, and the second portion of the lockable coupling mechanism. The feature for attaching the body to a respective vertebrae may include a pedicle screw or, alternatively, a shape such as a hook adapted for sublaminar engagement. The elongated element also preferably includes a length adjustment mechanism, such as a telescoping or threaded section to provide a desired length in conjunction with a desired degree of alignment. Various coupling mechanisms are disclosed to provide multiple degrees of freedom prior to fixation.

64 Claims, 38 Drawing Sheets

U.S. PATENT DOCUMENTS

| | | | |
|---|---|---|---|
| 5,312,405 A | 5/1994 | Korotko et al. | 606/61 |
| 5,330,473 A | 7/1994 | Howland | |
| 5,375,823 A | 12/1994 | Navas | |
| 5,387,213 A | 2/1995 | Graf et al. | |
| 5,466,237 A | 11/1995 | Byrd, III et al. | 606/61 |
| 5,474,555 A | 12/1995 | Puno et al. | 606/73 |
| 5,478,340 A | 12/1995 | Kluger | |
| 5,480,401 A | 1/1996 | Navas | |
| 5,536,268 A | 7/1996 | Griss | 606/61 |
| 5,540,688 A | 7/1996 | Navas | |
| 5,545,166 A | 8/1996 | Howland | |
| 5,607,425 A | 3/1997 | Rogozinski | |
| 5,624,442 A | 4/1997 | Mellinger et al. | 606/61 |
| 5,630,816 A | 5/1997 | Kambin | |
| 5,643,264 A | 7/1997 | Tai et al. | |
| 5,645,544 A | 7/1997 | Sherman et al. | |
| 5,665,122 A | 9/1997 | Kambin | |
| 5,667,508 A | 9/1997 | Errico et al. | 606/73 |
| 5,669,911 A | 9/1997 | Errico et al. | 606/61 |
| 5,672,176 A | 9/1997 | Biedermann et al. | 606/61 |
| 5,676,665 A | 10/1997 | Bryan | 606/61 |
| 5,690,630 A | 11/1997 | Errico et al. | 606/61 |
| 5,704,936 A | 1/1998 | Mazel | |
| 5,716,355 A | 2/1998 | Jackson et al. | 606/61 |
| 5,725,527 A | 3/1998 | Biedermann et al. | 606/61 |
| 5,776,135 A | 7/1998 | Ralph et al. | |
| 5,800,435 A | 9/1998 | Tatar et al. | |
| 5,863,293 A | 1/1999 | Richelsoph | |
| 5,873,878 A | 2/1999 | Harms et al. | 606/61 |
| 5,928,232 A | 7/1999 | Tebbe et al. | |
| 5,928,237 A | 7/1999 | Bonner et al. | |
| 5,938,663 A | 8/1999 | Petreto | 606/61 |
| 5,944,719 A | 8/1999 | Leban | |
| 5,944,720 A | 8/1999 | Lipton | |
| 5,947,966 A | 9/1999 | Drewry et al. | 606/61 |
| 5,951,555 A | 9/1999 | Cech et al. | |
| 5,954,725 A | 9/1999 | Drewry et al. | |
| 5,961,516 A | 10/1999 | Graf | |
| 5,980,523 A | 11/1999 | Jackson | 606/61 |
| 6,063,089 A | 5/2000 | Ralph et al. | |
| 6,074,391 A | 6/2000 | Metz-Stavenhagen et al. | 606/61 |
| 6,113,600 A | 9/2000 | Sherman et al. | |
| 6,136,003 A | 10/2000 | Hoeck et al. | 606/61 |
| 6,139,548 A | 10/2000 | Errico | 606/61 |
| 6,190,388 B1 | 2/2001 | Boyd et al. | |
| 6,217,578 B1 | 4/2001 | Crozet et al. | 606/61 |
| 6,224,598 B1 | 5/2001 | Jackson | 606/61 |
| 6,234,705 B1 | 5/2001 | Troxell | 403/237 |
| 6,241,730 B1 | 6/2001 | Alby | |
| 6,264,658 B1 | 7/2001 | Choi et al. | |
| 6,267,765 B1 | 7/2001 | Villaret et al. | |
| 6,273,914 B1 | 8/2001 | Papas | |
| 6,296,644 B1 | 8/2001 | Barbera Alacreu et al. | |
| 6,283,967 B1 | 9/2001 | Troxell et al. | 606/61 |
| 6,306,137 B2 | 10/2001 | Troxell | 606/61 |
| 6,325,802 B1 | 12/2001 | Frigg | 606/61 |
| 6,379,354 B1 | 4/2002 | Rogozinski | |
| 2001/0034521 A1 | 10/2001 | Bailey et al. | 606/61 |

OTHER PUBLICATIONS

Dipreta, "The Iliac Nail/Screw: A Modified . . . ", Am. Acad. of Ortho. Surg., 67th mtg.,PE 184, Mar. 19, 2000.

Erickson, "Biomechanical Assessment of . . . ", Am. Acad. of Ortho Surg., 2002 mtg., P217, Mar. 13, 2002.

Beadling, "Harrington put the steel in spinal fixation.", Orthopedics Today, Jun. 2000.

Hart, "Placement of Pedicle Screws in the Thoracic . . .", Am. Acad. of Ortho. Surg., PE 276, Mar. 4, 2001.

Wood, "Torsional Rigidity of Scoliosis Constructs.", Am. Acad. of Ortho. Surg., PE123, Feb. 4, 1999.

Pham, "Upper Cervical Spine Surgery in . . . ", Joint Bone Spine 2000, 67, 434–440.

Sanders, "Treating, managing spinal deformity in young patients." Orthopedics today, Jul. 2001.

Spiegel, "Anterior Instrumentation in the Treatment . . . ", U.P.O.J., vol. 11, Spring 1998, pp. 19–26.

International Search Report in PCT Counterpart Application PCT/US02/11301, (3 pages).

U.S. patent application Ser. No. 60/301,181, filed Jun. 27, 2001, Poyaxial Pedicle Screw (provisional application).

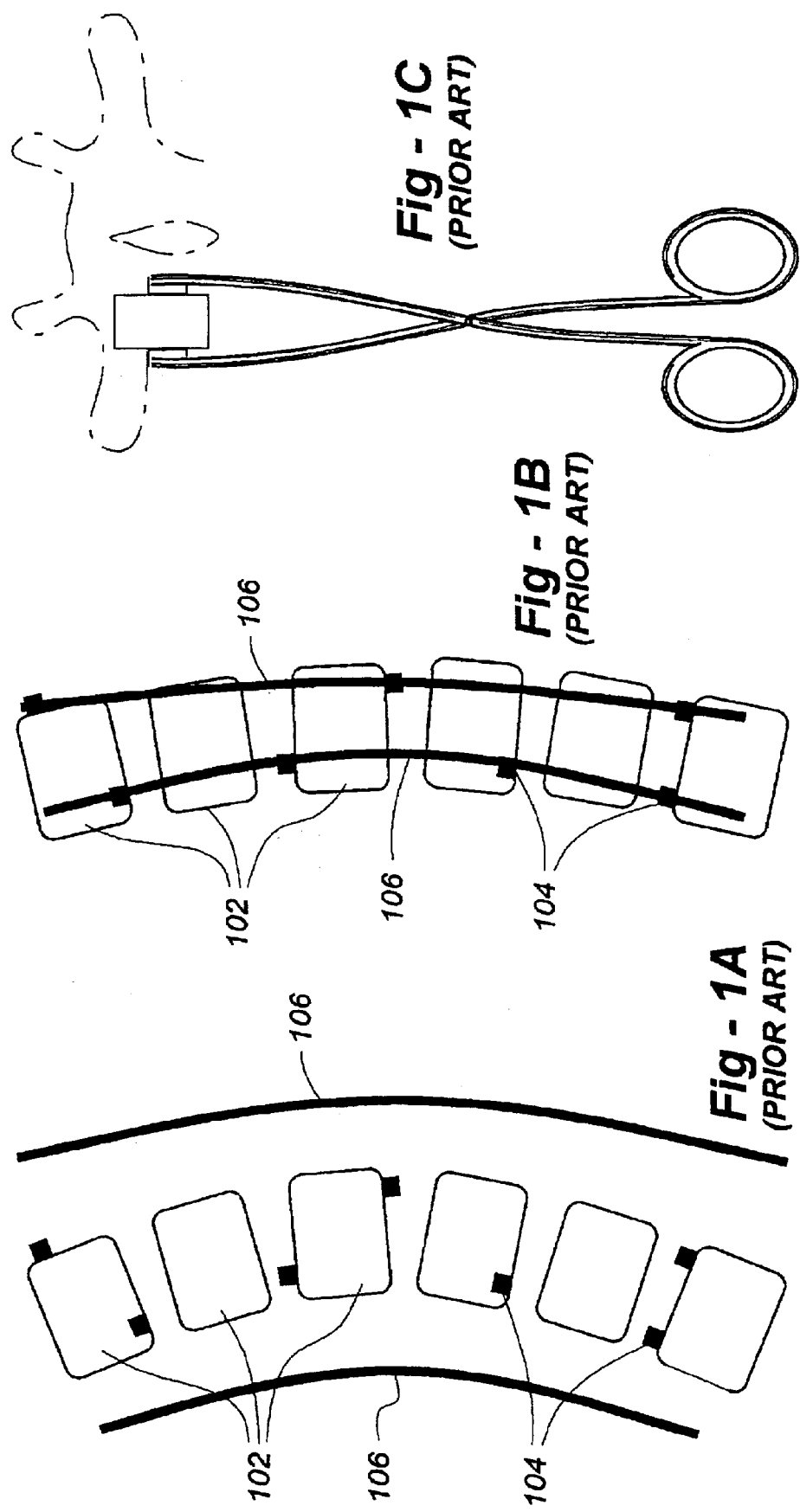

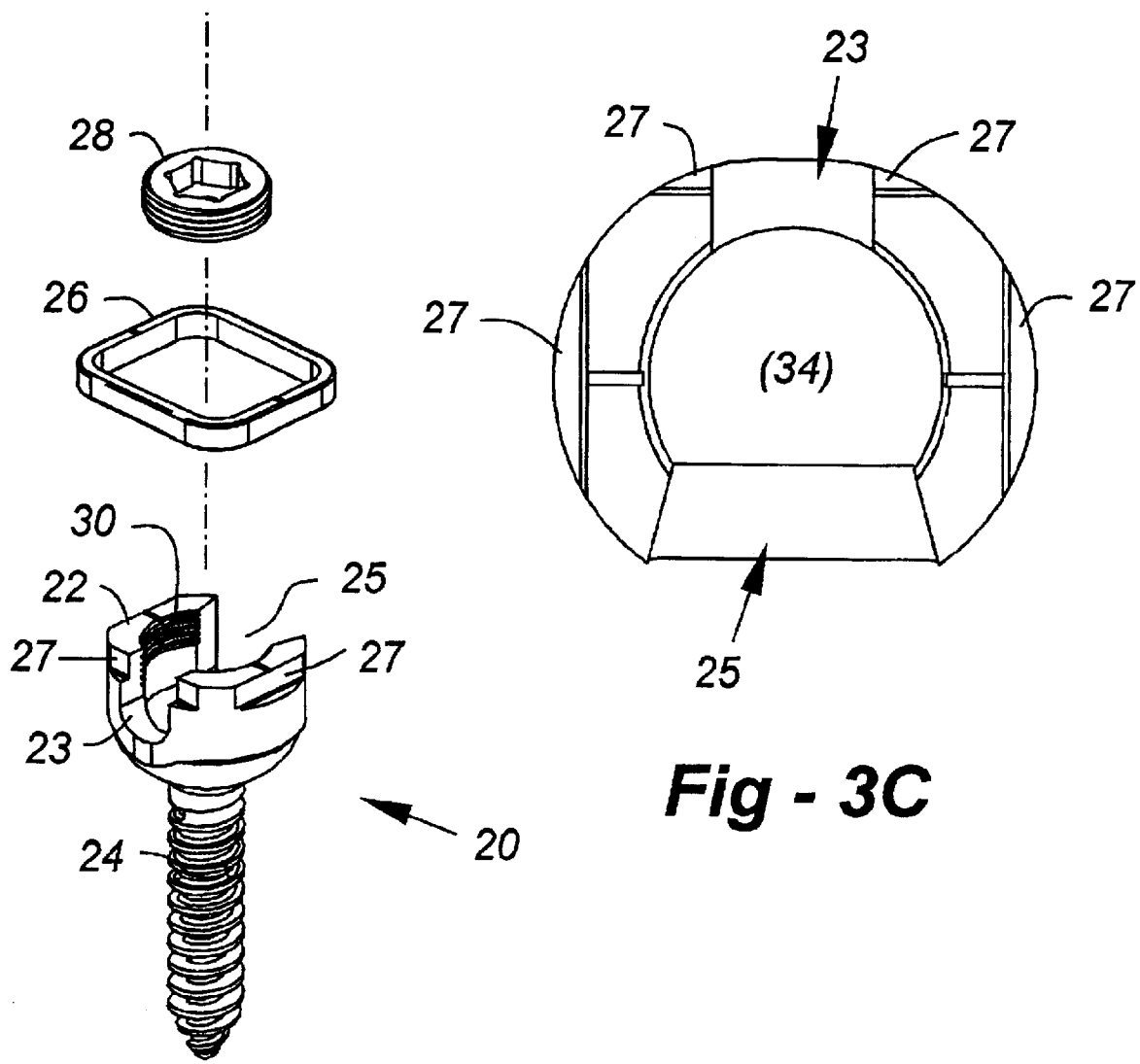

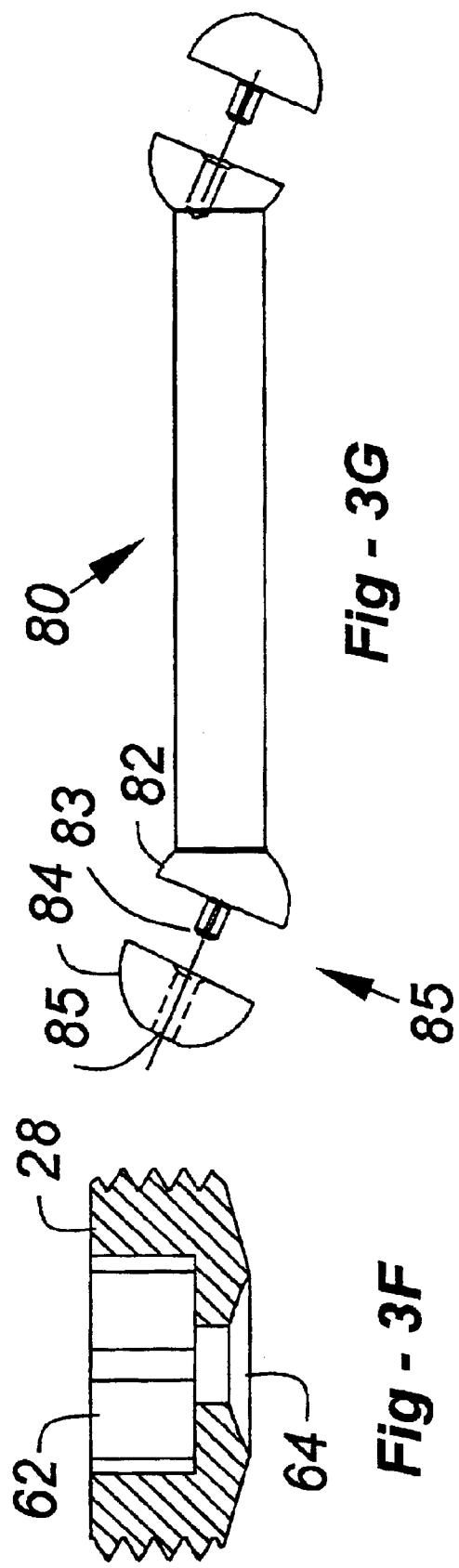

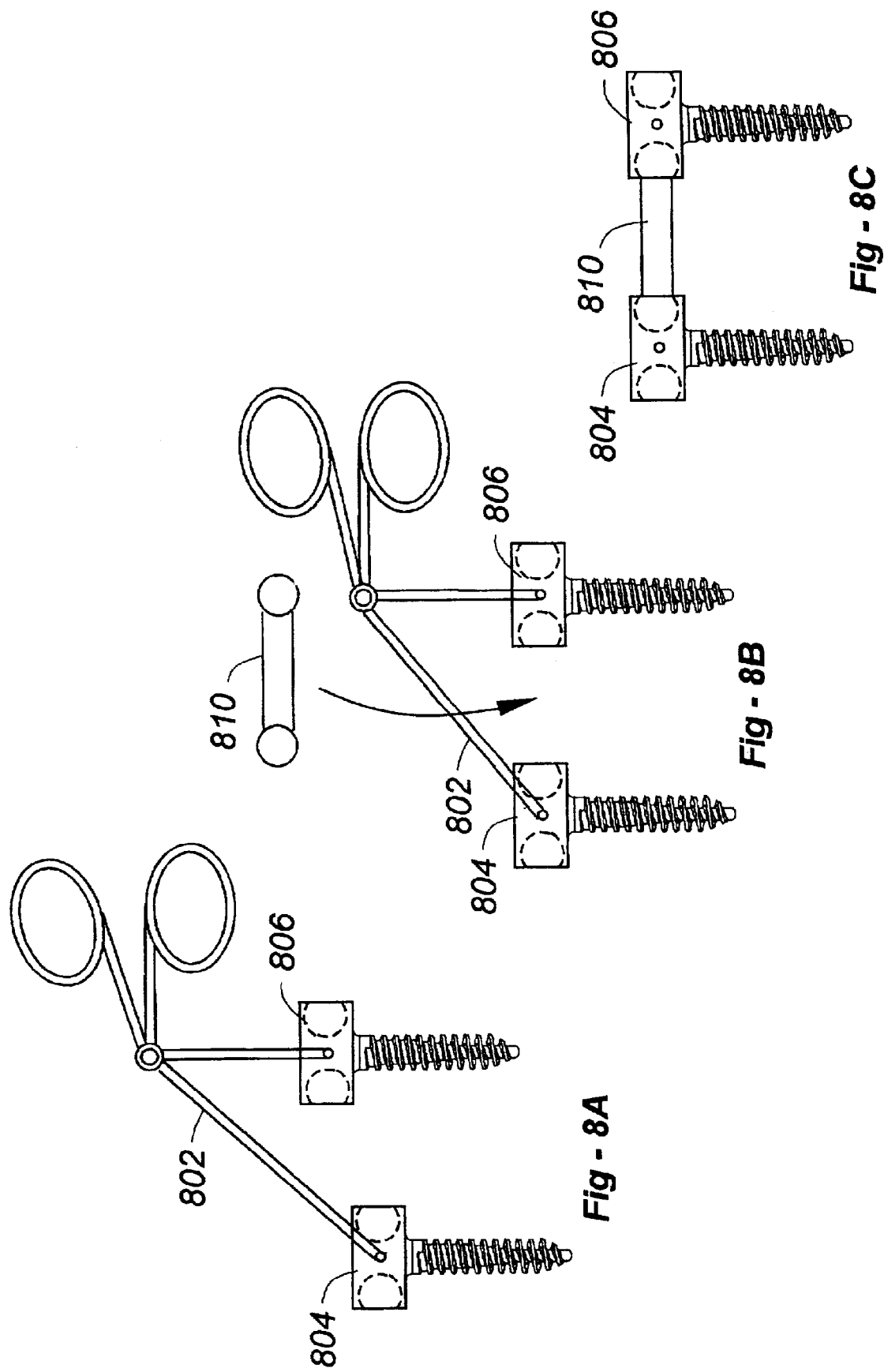

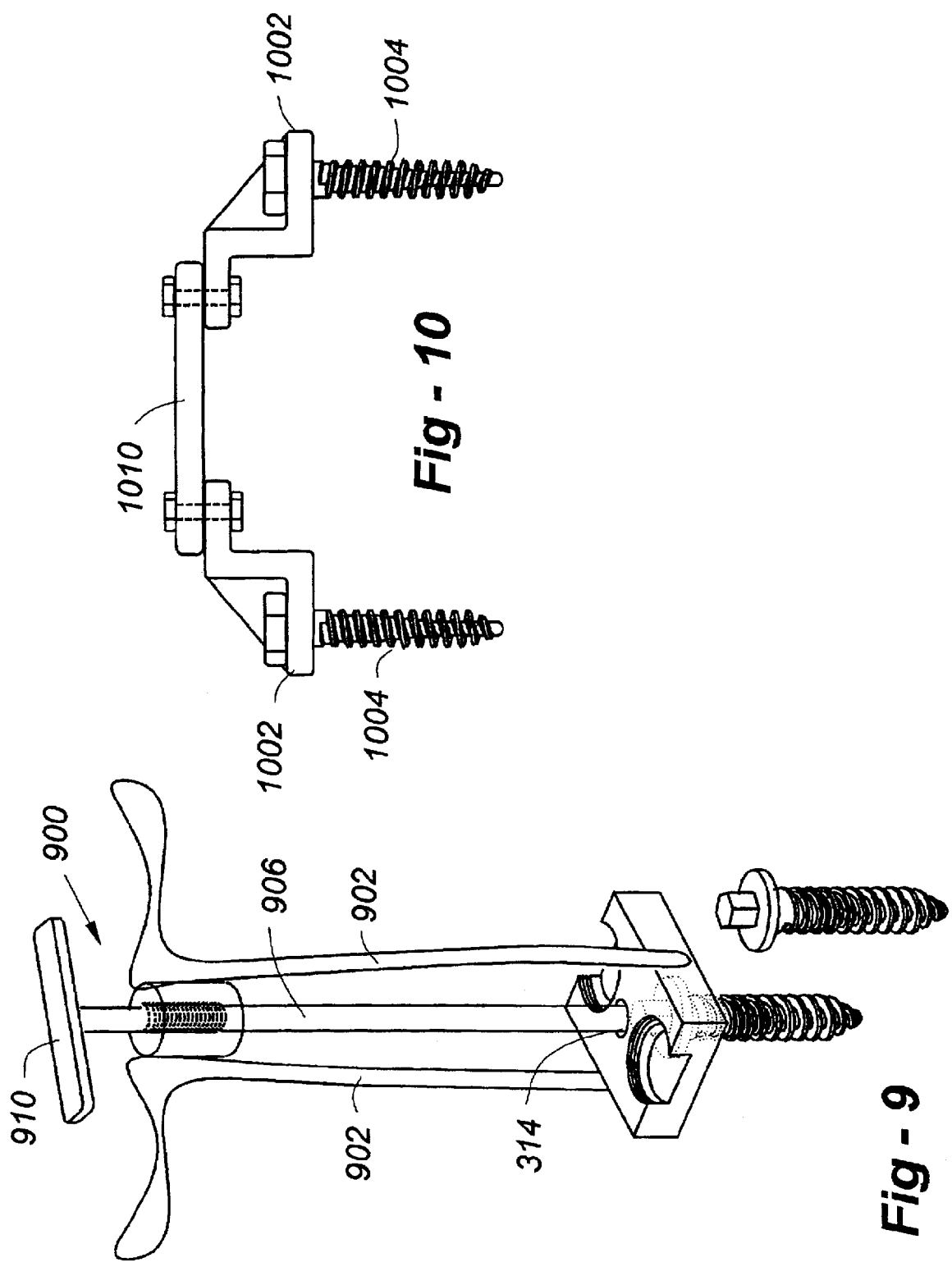

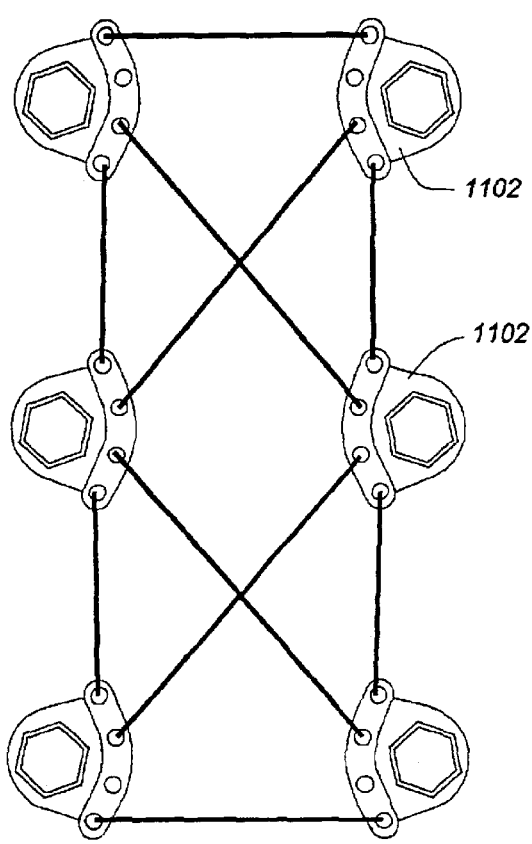
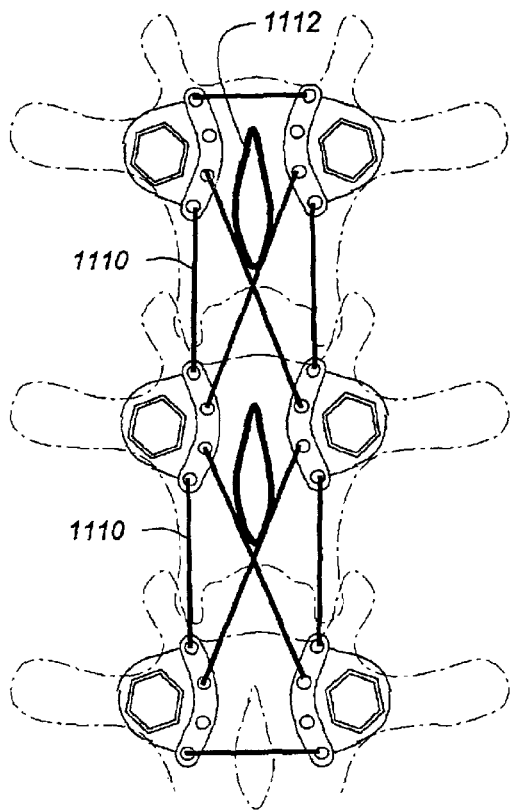
Fig - 11A
Fig - 11B
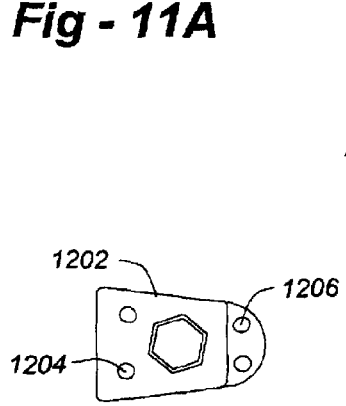
Fig - 12A
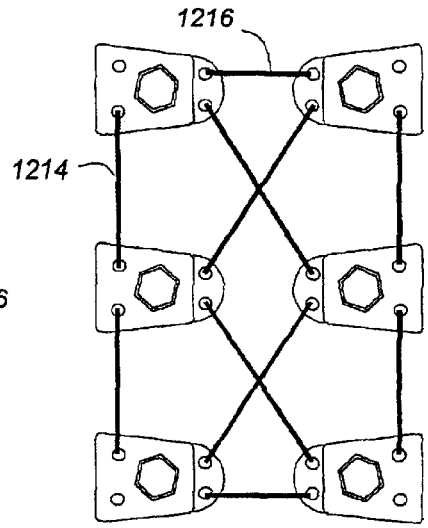
Fig - 12B
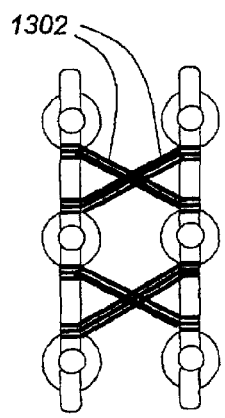
Fig - 13

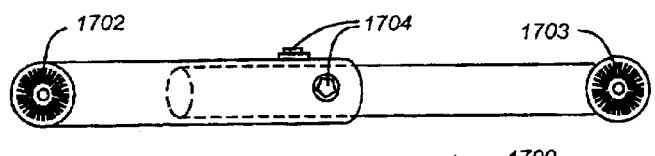
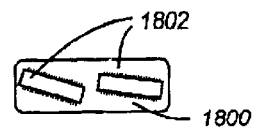
Fig - 17
Fig - 18B
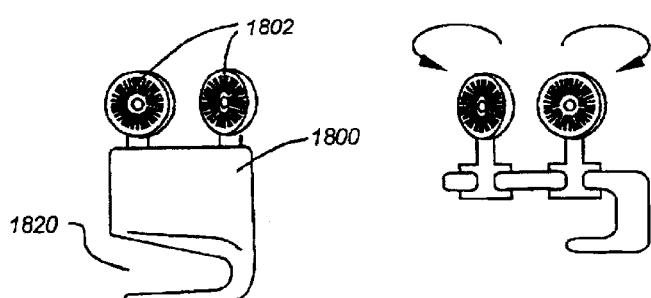
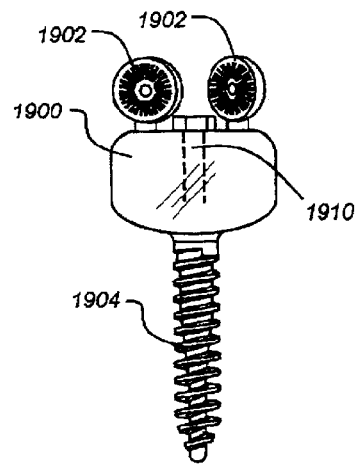
Fig - 18A
Fig - 18C
Fig - 19
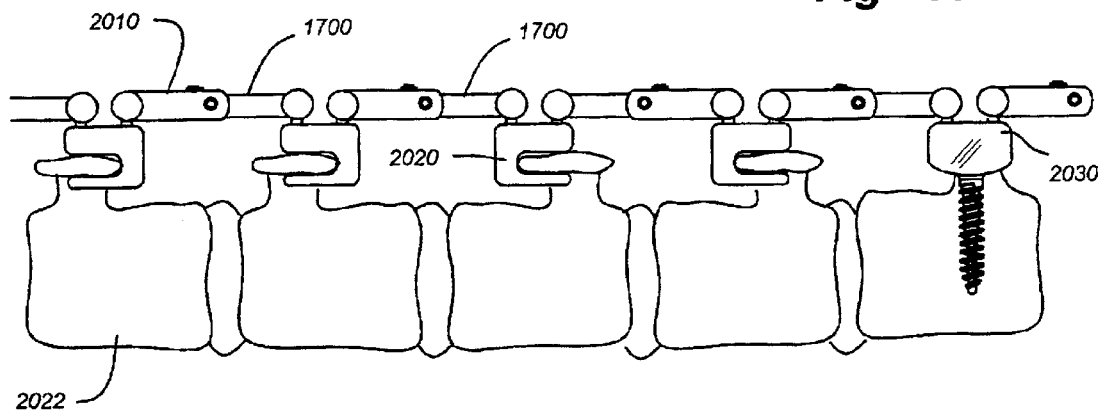
Fig - 20

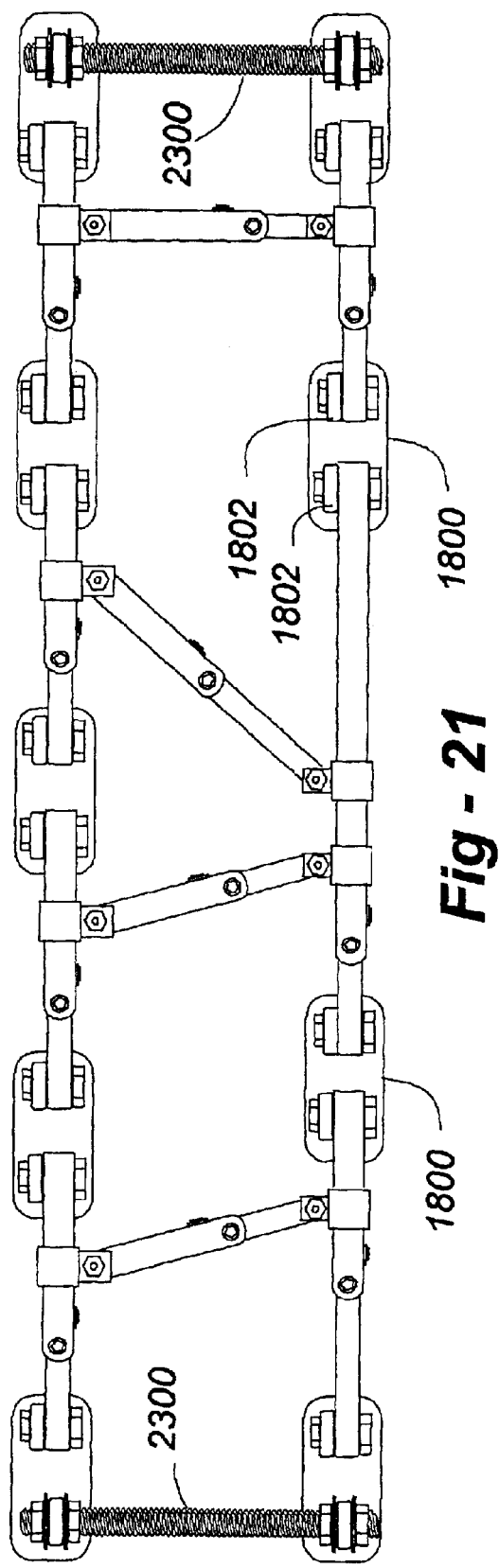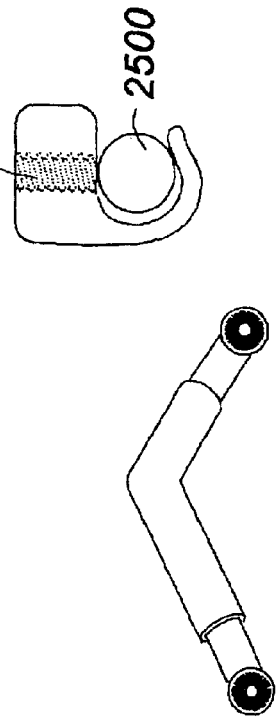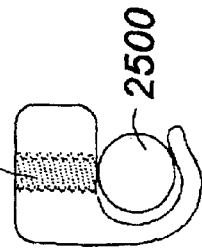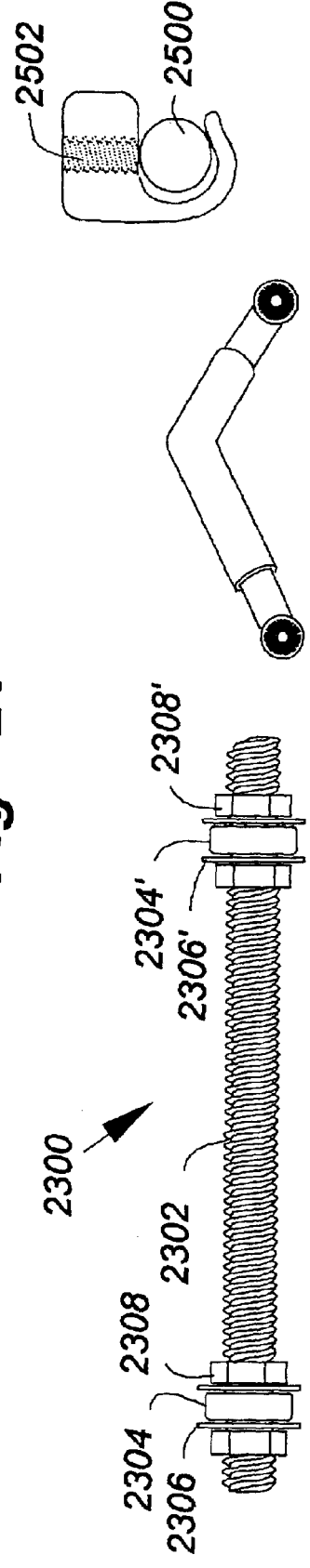

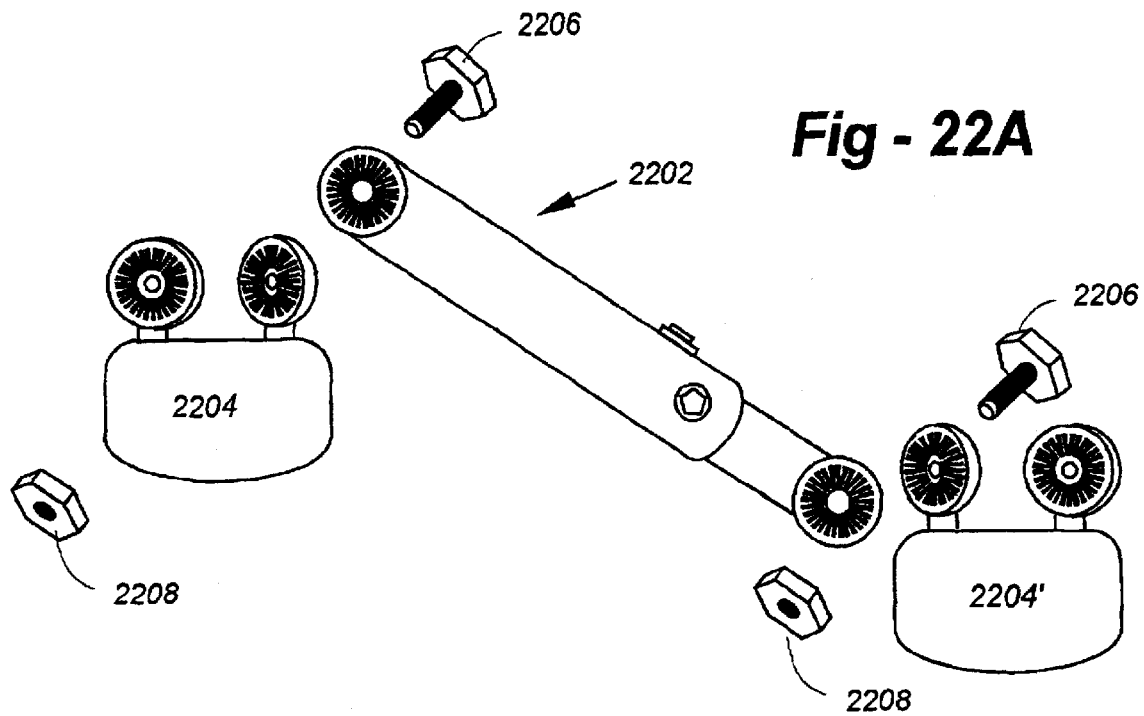
Fig - 22A
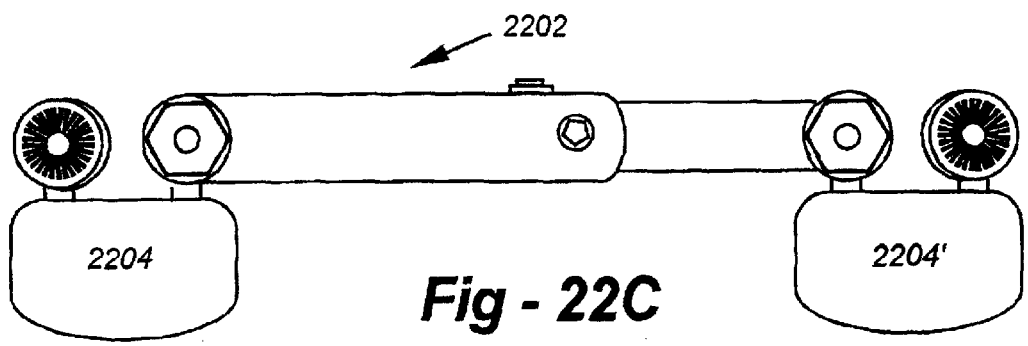
Fig - 22B
Fig - 22C

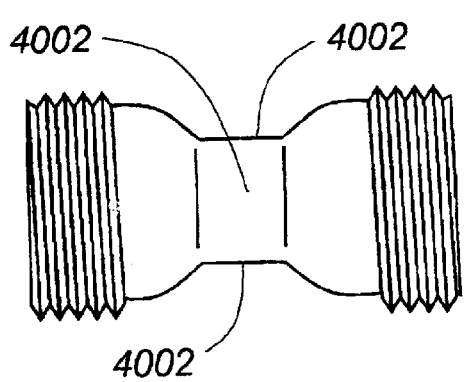
Fig - 40A
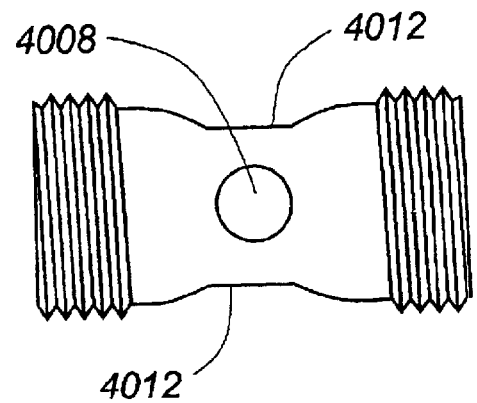
Fig - 40B
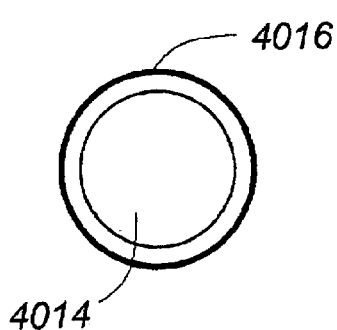
Fig - 40C
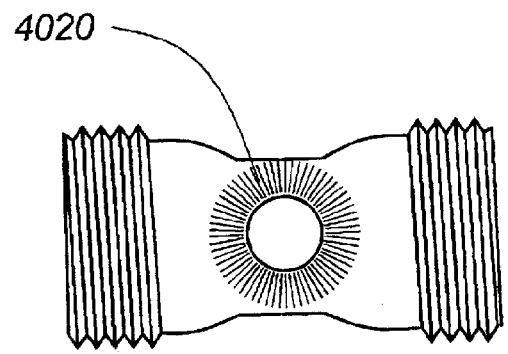
Fig - 40D
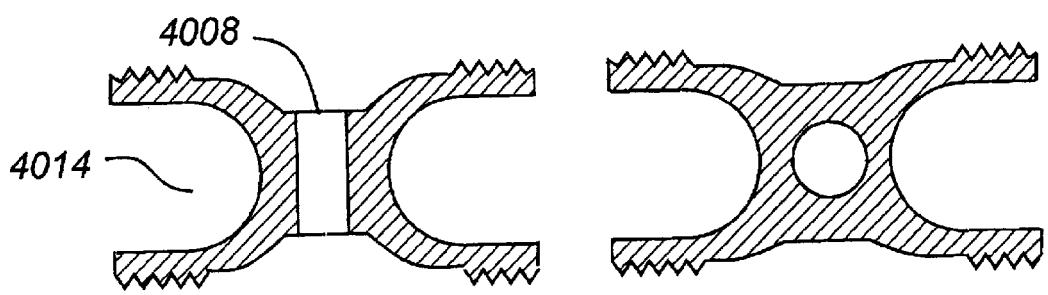
Fig - 40E  Fig - 40F

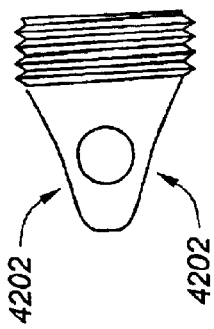
*Fig - 42B*
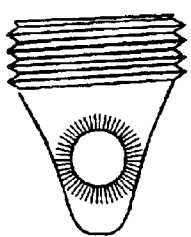
*Fig - 42D*
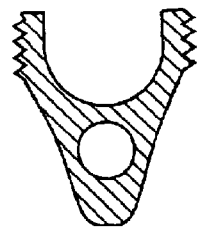
*Fig - 42E*
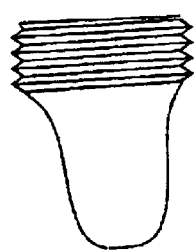
*Fig - 42A*
*Fig - 42C*
*Fig - 41G*
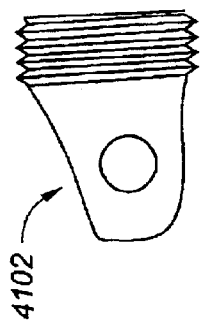
*Fig - 41B*
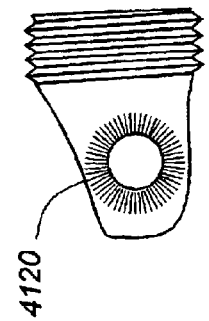
*Fig - 41D*
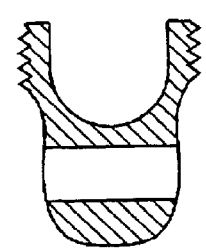
*Fig - 41F*
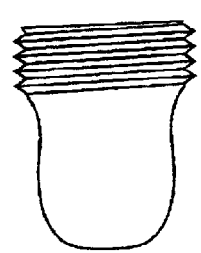
*Fig - 41A*
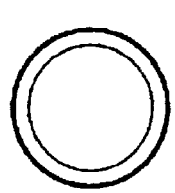
*Fig - 41C*
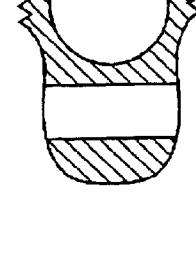
*Fig - 41E*

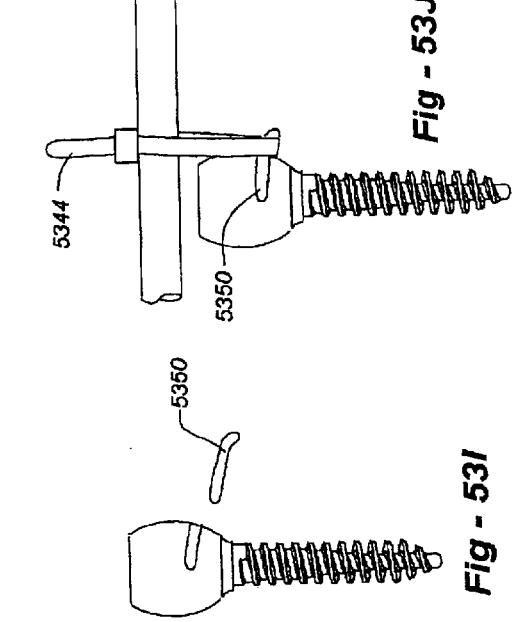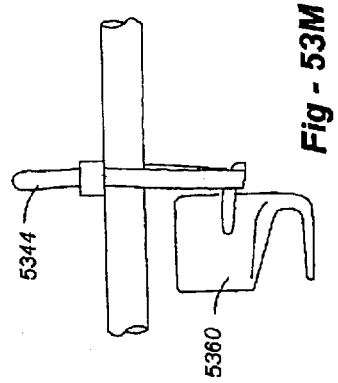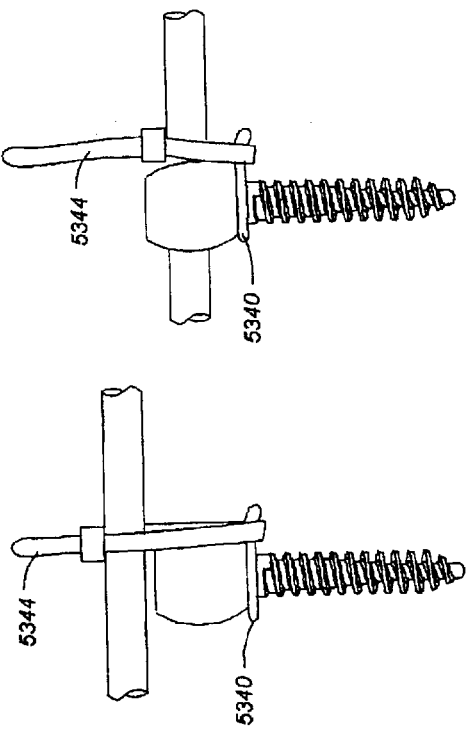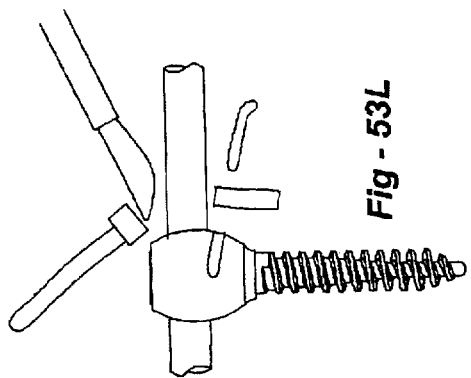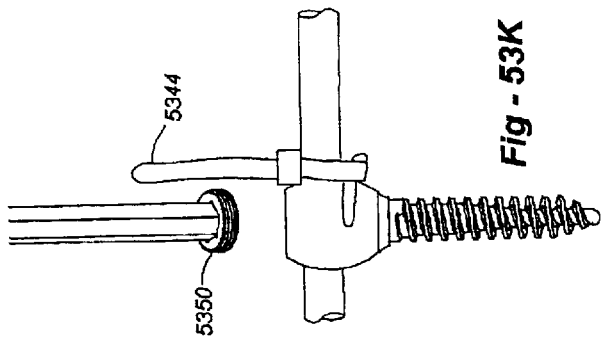

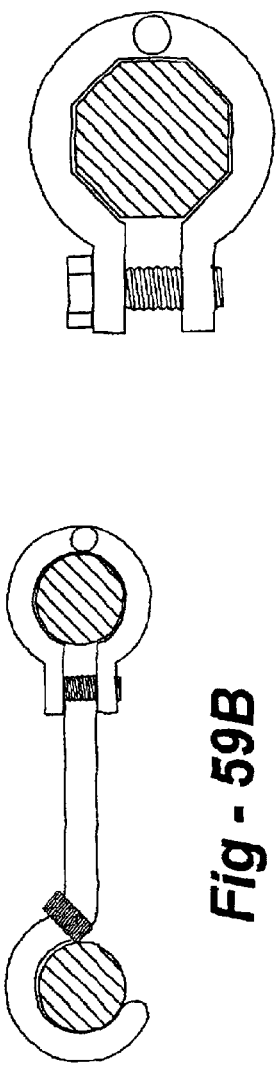
*Fig - 61*
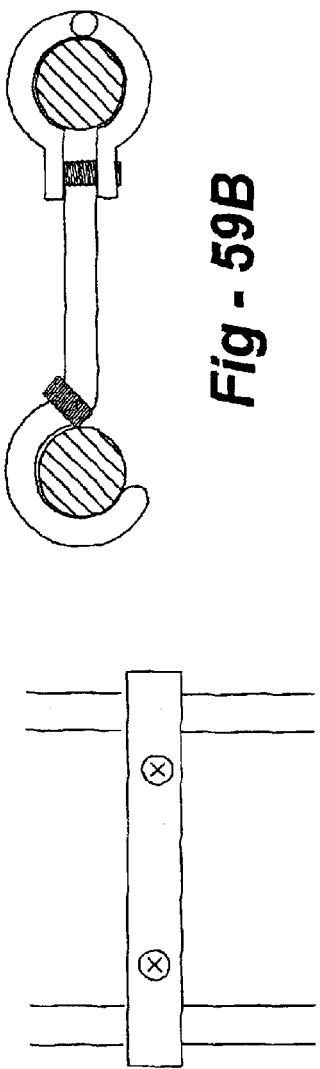
*Fig - 59B*
*Fig - 59A*
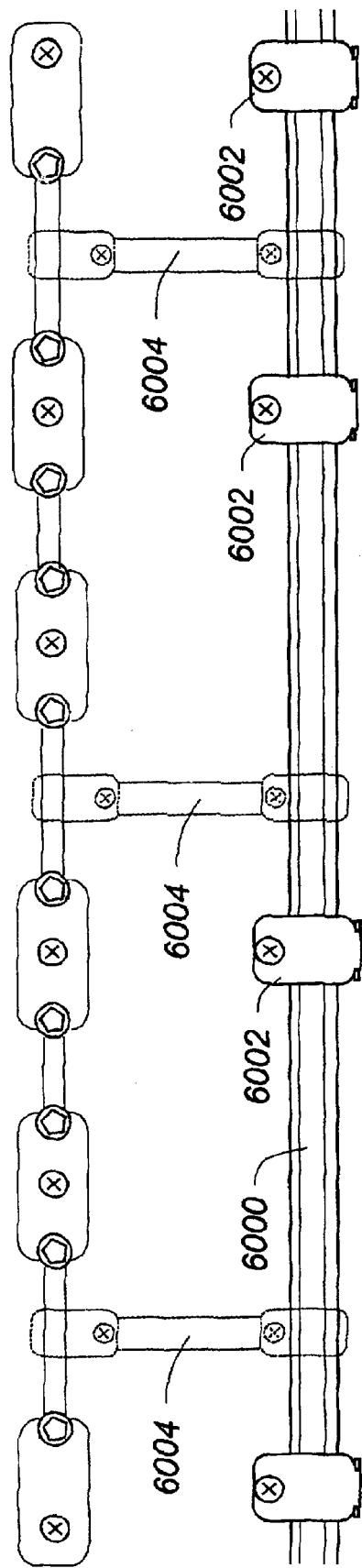
*Fig - 60*

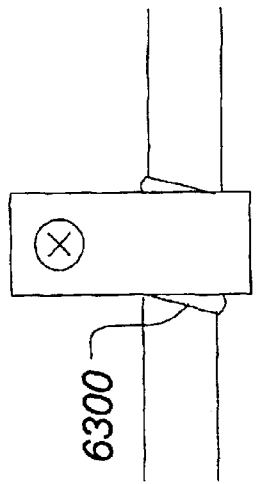
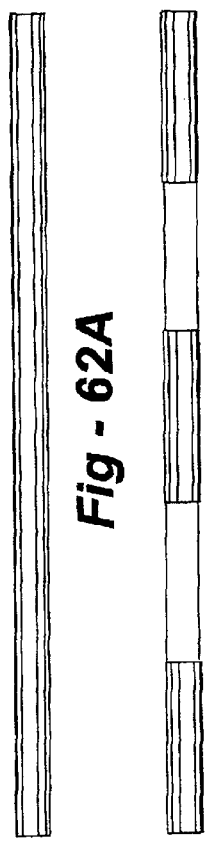
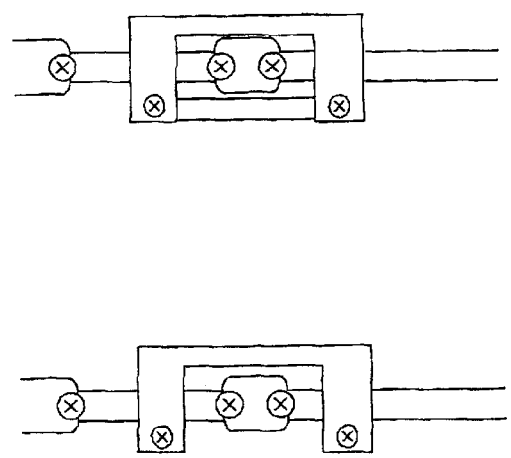
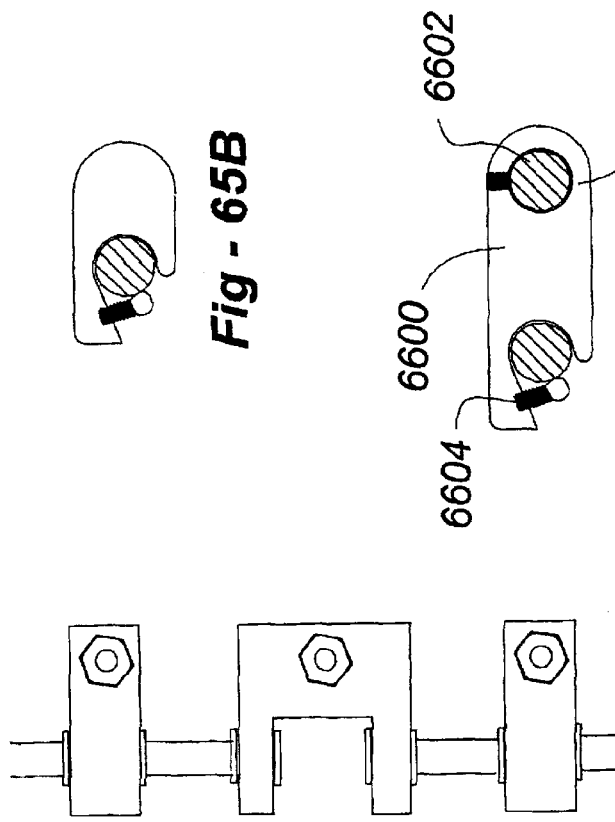

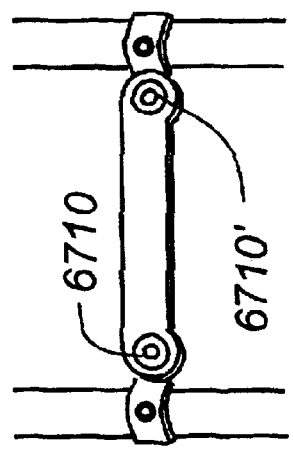
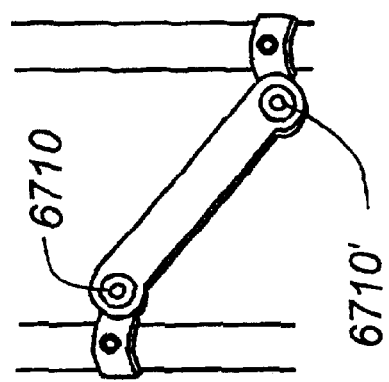
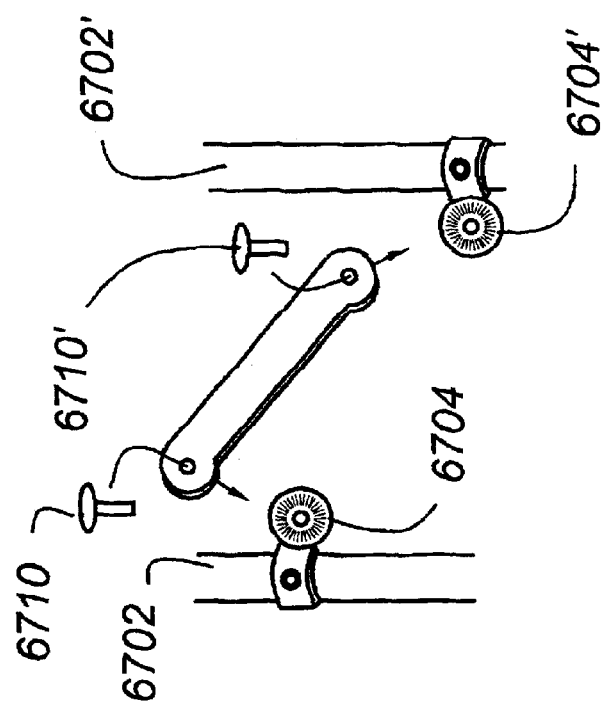
Fig - 67C
Fig - 67B
Fig - 67A

SPINAL ALIGNMENT APPARATUS AND METHODS

REFERENCE TO RELATED APPLICATION

This application claims priority from U.S. provisional patent application Ser. No. 60/278,910, filed Mar. 26, 2001, the entire contents of which being incorporated herein by reference.

FIELD OF THE INVENTION

This invention relates generally to instrumentation, tools and techniques associated with spinal fixation and, in particular, to apparatus and methods facilitating spinal correction in multiple dimensions.

BACKGROUND OF THE INVENTION

The human spine exhibits some degree of curvature at different levels to facilitate normal physiologic function. Correction may be required when this curvature deviates substantially. A common problem is lateral deviation of the spine, commonly termed scoliosis.

Spinal deformity occurs when a patient has abnormal frontal or sagittal plane alignment. At the same time, the cervical and lumbar spine exhibit lordosis, while the thoracic spine has kyphosis. Thus, when performing spinal fusion, surgeons may be required to preserve or restore both front plane and sagittal alignment while taking lordosis and kyphosis into account.

As discussed in U.S. Pat. No. 5,540,689, the first successful internal fixation method for surgically treating scoliosis used the Harrington instrumentation system. According to this technique, a rigid rod with hooks at each end is implanted adjacent the concave side of the scoliotic spine. The spine is manually straightened to a desired extent and a distraction rod is used to maintain the correction by exerting vertical forces at each end. The rod commonly has a ratcheted end over which hooks are slidably mounted and locked in place. To accommodate lordosis, a compression rod is sometimes placed on the convex side of the scoliotic spine.

The Harrington instrumentation system has been used successfully for some time, but because the distraction rod is fixed to the spine in only two places, failure at either end causes the entire system to fail. Another deficiency with existing mechanisms and approaches is that the single rod used to correct the defects must be contoured to fit various attachment sites. In patients having compound spinal deformity, this may be extremely difficult. A further problem is that the contoured rod frequently limits further correction of certain types of deformities. That is, once the rod is in position, further correction of the deformity is difficult, since existing systems tend to limit incremental alignment procedures.

An alternative treatment has since evolved which takes advantage of segmented fixation. According to this method, a rod is fixed to the spine at multiple points by means of sublaminar wires which run underneath the lamina of the vertebra an around the rod. The use of multiple fixation sites enhances stability and reduces the need for additional post-operative bracing.

Sublaminar fixation utilizing current devices has two primary weaknesses, however. First, the wires are simply wrapped around the rod, resulting in a rod to cable junction which is not rigid. Second, the thin wires can cut in some instances right through the lamina.

U.S. Pat. No. 6,019,759 uses multiple longitudinal members with at plates that attach using hooks or screws. However, the plates are stacked on top of one another at each attachment site, resulting in an overall structure that tends to be quite thick. Systems having a high sagittal profile are often thick enough to be felt through the skin. Additionally, the teaching of the '759 patent do not allow for easy correction or preservation of sagittal alignment.

The need remains, therefore, for a system and method that allows incremental correction of spinal defects, ideally in all three dimensions.

SUMMARY OF THE INVENTION

This invention resides in spinal alignment apparatus, including implantable components, instrumentation, and methods of use. In broad and general terms, the preferred embodiment includes bodies which connect to the vertebra to be aligned, and elongated elements that connect to the bodies. The elements are preferably adjustable relative to the bodies in multiple dimensions, with locking mechanisms that allow the alignment to proceed in an orderly fashion until a desired degree of correction is achieved.

Each rigid, elongated element has at least one end terminating in the first portion of the lockable coupling mechanism. The vertebral connector bodies each include a feature for attaching the body to a respective vertebrae, and the second portion of the lockable coupling mechanism. This arrangement permits the elongated elements to be adjusted in multiple dimensions relative to a given connector body prior to being lockingly coupled thereto.

The feature for attaching the body to its respective vertebrae may include a pedicle screw or, alternatively, a shape such as a hook adapted for sublaminar engagement. The elongated elements may also preferably include a length adjustment mechanism, such as a telescoping or threaded section, to provide a desired length in conjunction with a desired degree of alignment.

Various coupling mechanisms are disclosed to provide multiple degrees of freedom prior to fixation. In the preferred embodiment, the mechanism includes a fixed or adjustable-length rod having ball-shaped ends coupled to a vertebral connector providing multiple degrees of freedom before being locked into position once a desired orientation is achieved.

BRIEF DESCRIPTION OF THE DRAWINGS

FIG. 1A is a frontal view of elongated rods and hooks currently used to correct spinal defects;

FIG. 1B shows the use of two rods in place, attached to multiple vertebrae;

FIG. 1C illustrates the way in which a typical prior-art hook is positioned under the spinal lamina for rod insertion;

FIG. 3B is a detail drawing of a single-opening pedicle screw according to the invention;

FIG. 3C is a top-down view of the single-opening pedicle screw of FIG. 3B;

FIG. 3F is a drawing that shows a preferred set-screw fastener according to the invention for use with the single- and multi-opening fasteners of FIGS. 3A through 3E;

FIG. 3G is a drawing which shows the way in which caps may be added to elongated members according to the invention to produce spherical or semi-spherical endings;

FIG. 3H is a drawing which shows the way in which multiple elongated members may be interconnected to produce a single spherical or semi-spherical joint region;

FIG. 8A illustrates a first step associated with restoring sagittal alignment;

FIG. 8B shows two vertebrae with appropriate sagittal alignment in preparation for rod insertion;

FIG. 8C shows the vertebrae of FIGS. 8A and 8B, with a linking rod in place and a tool and the tool removed;

FIG. 9 illustrates the use of a tool used to remove a connector from a ball-tip type of pedicle screw according to the invention;

FIG. 10 is a drawing of an alternative embodiment of the invention, wherein connectors include multiple apertures for linking bars;

FIG. 11A shows the configuration of FIG. 10 with lines indicating a desired placement of cross-members;

FIG. 11B shows the linking members of FIGS. 10 and 11A with optional sublaminar cabling;

FIG. 12A is a drawing of an alternative connector having multiple apertures for linking bars or other elements;

FIG. 12B shows the alternative connector of FIG. 12A with lines indicating one possibility for cross-linking;

FIG. 13 is a drawing which shows the use of diagonal connectors according to the invention for use with existing rod- or plate-alignment systems;

FIG. 17 is a drawing which shows a telescoping rod that may be adapted for use with any of the embodiments described herein;

FIG. 18A is a drawing of a sublaminar hook having swivel connectors to which the ends of the telescoping rod of FIG. 17 may attach;

FIG. 18B is an top-down view of the hook of FIG. 18A;

FIG. 18C is a cross-sectional view of the hook of FIG. 18A;

FIG. 19 illustrates a pedicle-screw version of the hook of FIG. 18A, also including locking connectors that swivel;

FIG. 20 is a side-view of the spine utilizing hook and pedicle-screw connectors according to one embodiment of the invention;

FIG. 21 is a top-view drawing of the spine, showing the use of cross connectors employed in an angular fashion to maximize rigidity;

FIG. 22A is a drawing which shows the way in which a telescoping connector according to the invention is installed;

FIG. 22B illustrates an intermediate adjustment procedure associated with the use of a telescoping rod according to the invention;

FIG. 22C shows the telescoping rod locked into place once a desired level of alignment is achieved;

FIG. 23 is a drawing of a threaded cross-connector according to the invention;

FIG. 24 is a drawing of a telescoping rod according to the invention having an arch feature that allows placement over arched lamina;

FIG. 25 is a cross-sectional drawing of a transverse connector according to the invention associated with a rod junction;

FIGS. 40A–40F provide different views of a central lumbar connector according to the invention;

FIGS. 41A–41G depict different views of a lumbar connector adapted to the cephalad end;

FIGS. 42A–42E show different views of a thoracic connectors according to the invention;

FIGS. 53A–53M illustrate the alternative use of straps according to the invention for rod movement and stabilization;

FIGS. 59A and 59B are different views of a transverse connector according to the invention;

FIG. 60 shows the combined use of transverse connectors and hinged hooks which lock onto a solid rod;

FIG. 61 is a close-up, end view of a hinged connector associated with an octagonal rod;

FIG. 62A illustrates the use of a continuous shaped rod, in this case having a grooved cross-section;

FIG. 62B illustrates how the modification along the rod may be interrupted according to the invention;

FIG. 63 is a drawing which shows a bevel connector;

FIG. 64 illustrates the use of multiple rods on either side of the spine;

FIG. 65A is a drawing which shows a stabilization clamp for use with various embodiments disclosed herein;

FIG. 65B is an end of the configuration of FIG. 65A;

FIG. 66A is a different alternative embodiment of a stabilizing assembly;

FIG. 66B is a cross-section of the assembly of FIG. 66A; and

FIGS. 67A–67C illustrate the use of lockable swivel-type connectors which may be fastened to one or, preferably a pair, of alignment rods to provide a desired degree of alignment and correction.

DETAILED DESCRIPTION OF THE INVENTION

FIGS. 1A through 1C present simplified representations regarding the way in which prior-art hooks and rods are used to treat spinal deformities. FIG. 1A shows a plurality of vertebrae 102 in need of alignment. In accordance with existing practice, hooks 104 are fastened to the vertebrae at points deemed to be useful by the attending surgeon. Tools are used in an attempt to align the vertebrae, at which time rods 106 are contoured at the time of the procedure to engage with the hooks 104 to maintain a desired degree of straightening, as shown in FIG. 1B. FIG. 1C illustrates the way in which a typical prior-art hook is positioned under the spinal lamina for rod insertion.

Figure 2A:
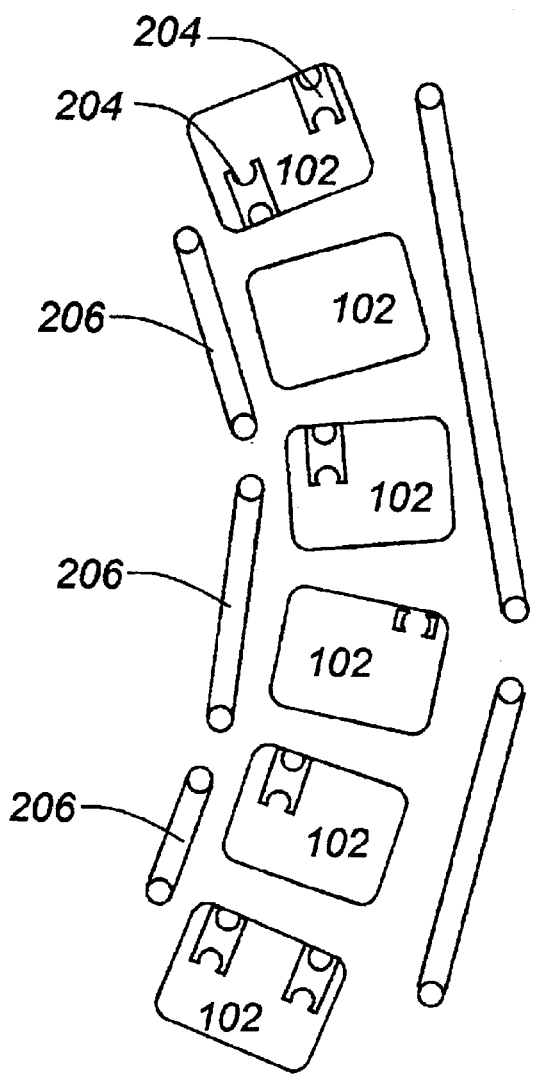
FIG. 2A is a frontal view of basic instrumentation according to the invention utilizing elongated members in the form of links of different length as opposed to longer rods.
Figure 2B:
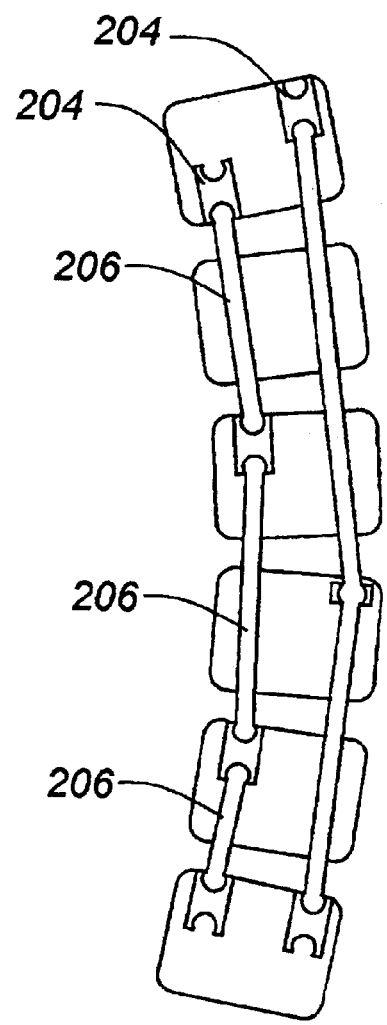
FIG. 2B shows the instrumentation of FIG. 2A in place relative to multiple vertebrae.

FIG. 2A illustrates basic instrumentation according to one embodiment of the invention. As opposed to the hooks 104 of prior-art devices, rotating/swiveling connectors 204 are instead used. In addition, as opposed to the rods 106 which currently must be contoured, links 206 of varying fixed or adjustable length are coupled to the connectors, and the entire structure locked into a preferred orientation, as shown in FIG. 2B. Although rotating/swiveling connectors having two rod-receiving positions are shown, the preferred embodiment of FIG. 3 shows how compound elements may be used for a single compression fitting and very low profile.

Figure 3A:
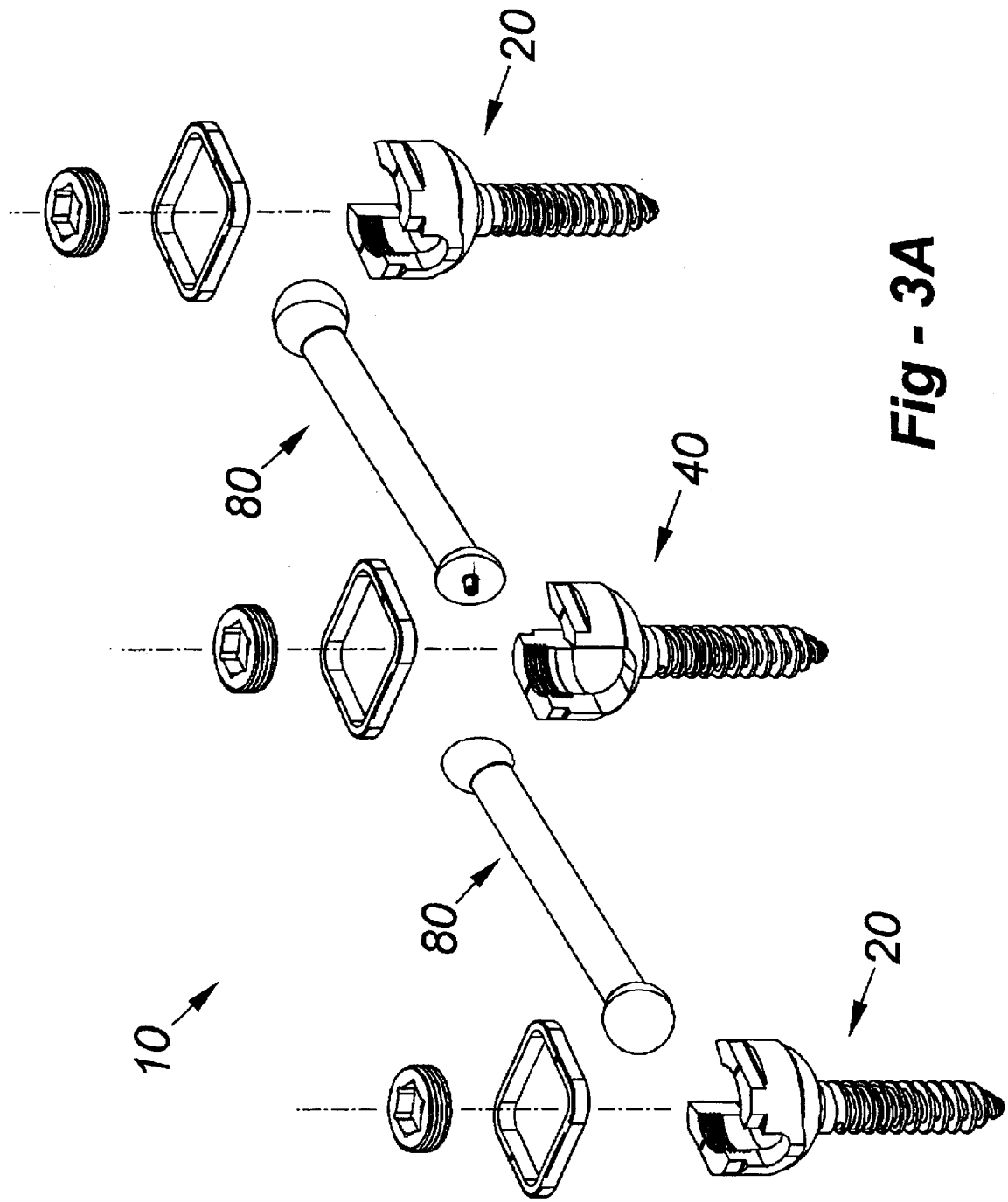
FIG. 3A illustrates components associated with a preferred embodiment of the invention, including a one- and multiple-opening pedicle screws, compound rods, tightening bands, and fasteners.

FIG. 3A illustrates a preferred system according to the invention, depicted generally at 10. Broadly, the system includes single-opening bodies 20, multiple-opening bodies 40, and rods 80. To afford additional degrees of freedom in multiple dimensions, the invention contemplates the use of rods having ball-shaped ends as well as the flattened plates of FIGS. 3I and 3J. Although the ball-shaped ends are shown as joinable to permit a single compression fastener as described below, it will be appreciated that solid members with integral spherical/shaped ends may be used, as well at the telescoping and other configurations disclosed with reference to the various alternative embodiments.

FIG. 3B is a detail drawing of a single-opening connector according to the invention, and FIG. 3C is a top-down view of the single-opening device of FIG. 3B. The structure 20 includes a rod-receiving body 22 coupled to a pedicle screw 24. The body includes one opening 23 configured for a constrained connection and a second opening 25 adapted for multiple degrees of freedom before compression fastener 28 is tightened into threaded area 30. To provide a solid mass, tension band 26 is positioned onto recesses 27 before tightening fastener 28. FIG. 3C shows the recesses 27 from above, as well as the bottom of hemispherical well 34 within the body 22.

Figures 3D, 3E:
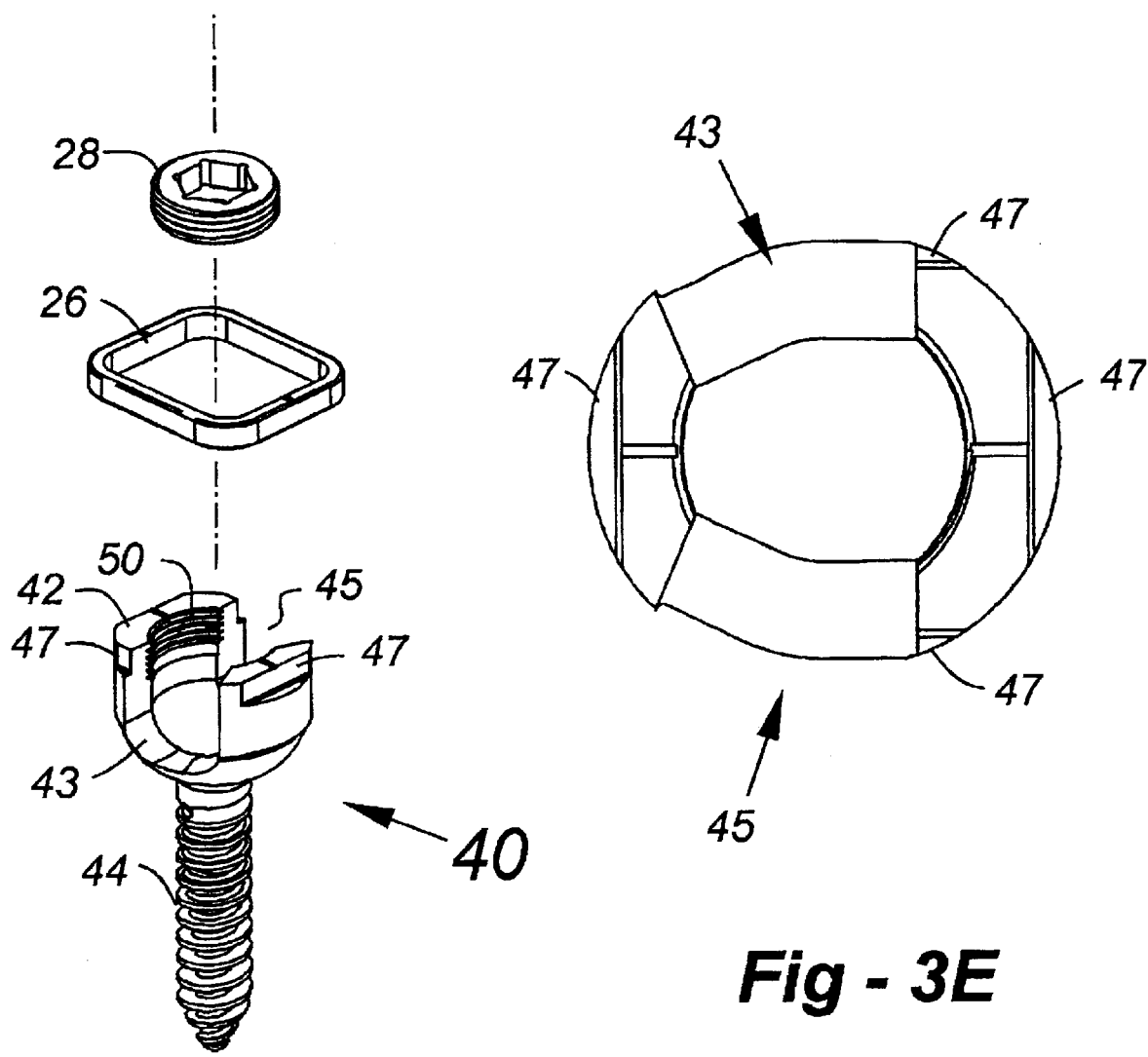
FIG. 3D is a detail drawing of a multi-opening pedicle screw according to the invention.
FIG. 3E is a top-down view of the multi-opening pedicle screw of FIG. 3D.

FIG. 3D is a detail drawing of a multiple-opening connector 40 according to the invention, and FIG. 3E is a top-down view of the multi-opening device 40 FIG. 3D, in this case a two-port device. The structure 30 includes a rod-receiving body 42 coupled to a pedicle screw 44. The body 42 includes one opening 43 configure for a first rod moveable in multiple dimensions, and a second opening 45 for a second rod, also adapted for multiple degrees of freedom before compression fastener 28 is tightened into threaded area 50. To provide a solid mass, a tension band 26 is positioned onto recesses 47 before tightening fastener 28. FIG. 3E shows the recesses 47 from above, as well as the bottom of hemi-spherical well with the body 42. Note that in the preferred embodiment the same tightening band 26 and set screw 28 may be used for both the single and multiple opening configurations.

FIG. 3F is a cross-sectional drawing of the preferred compression fastener, in this case a set screw 28 having an allen-wrench-receiving top portion 62 and a hemispherical bottom portion 64.

FIG. 3G is a drawing which shows the way in which caps may be added to elongated members according to the invention to produce spherical or semi-spherical endings. FIG. 3H is a drawing which shows the way in which multiple elongated members may be interconnected to produce a single spherical or semi-spherical joint region. In the preferred embodiment, link members 80 have male/female half spheres allowing either caps or additional rods to be attached. This not only reduces the number of devices on the surgeons tray, it also allows two rods to form a single ball unit for a smaller profile.

In FIG. 3G, end 82 includes a male post 83, which receives end cap 84 having female aperture 85. The other end of the rod functions in like manner, with the male and female roles reversed. Although the posts and apertures are not technically necessary, they do allow the surgeon to pre-assemble components which hold together prior to installation, thereby maximizing the use of both hands. As shown in FIG. 3H, two rods may be connected to one another as opposed to the end caps, thereby allowing the fastener of FIGS. 3D and 3E to have rods extending from both sides. Note that the rods of FIG. 3H may be turned at the joint region prior to installation, thereby permitting the rods to extend from the connector of FIGS. 3D and 3E at various angles prior to tightening.

Figure 3I:
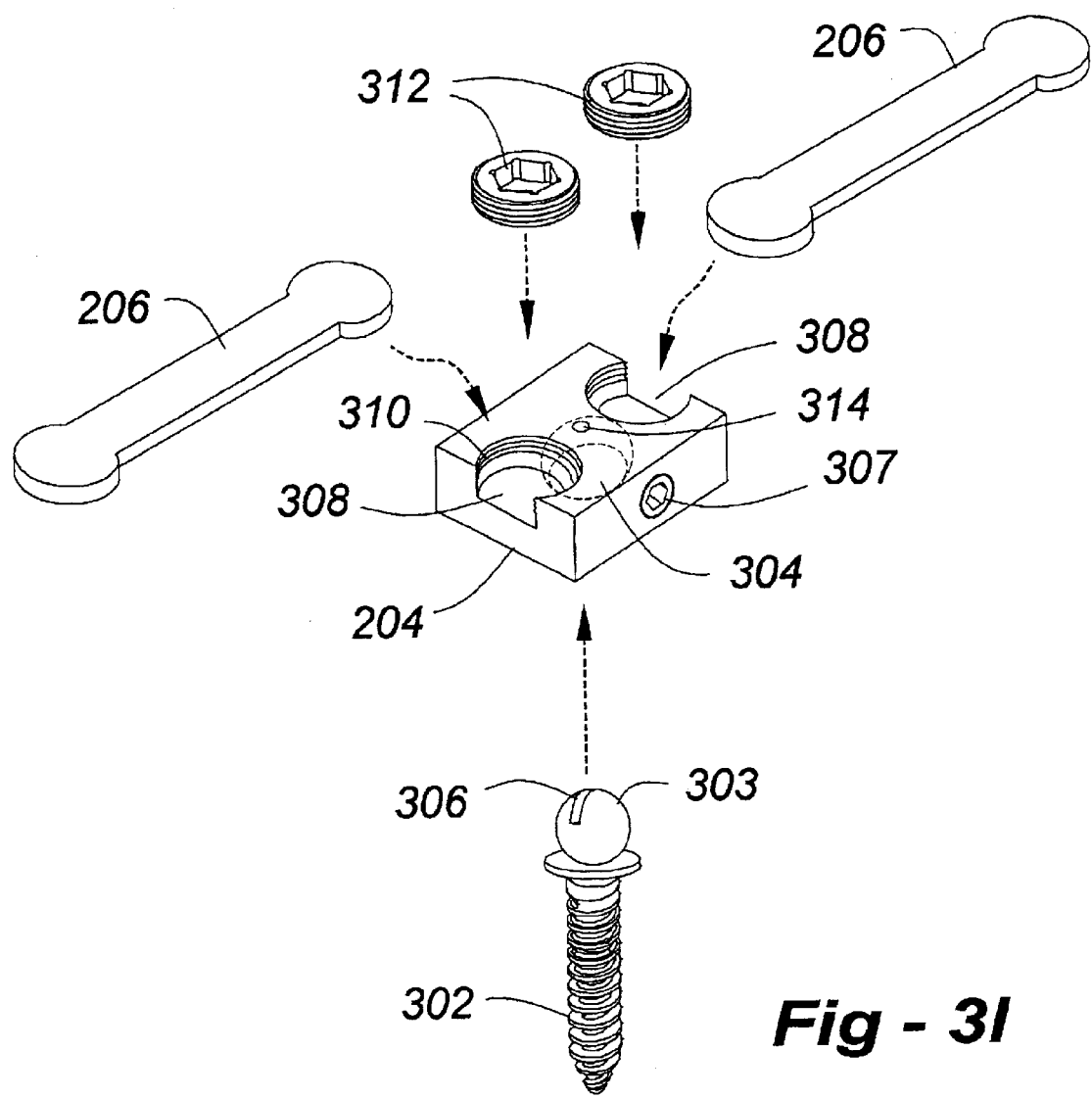
FIG. 3I illustrates components associated with an alternative embodiment of the invention, including a pedicle screw, swivel connector and locking links.

FIG. 3I illustrates an alternative connector system according to the present invention. A pedicle screw 302 having a hemispherical head 303 and a slot 306 (or alternatively a hex head or other suitable tool-engaging feature) is driven into the vertebrae at points useful for alignment. A connector body 204 is placed over the exposed end of the screw 302 so that the head 303 engages with a corresponding opening 304 in the bottom of the connector. A set screw 307 or other fastener is used to lock th body 204 in place relative to screw 302 and vertebrae to which it is attached. At this point, the body 204 is able to swivel in three dimensions until the devices are locked into place.

Link bars 206, preferably with enlarged ends are placed into recesses 308 into the body 204, and these are locked into place with set screws 312 or other suitable fasteners. Again, until the set screws 312 are tightened down, the links 206 may have at least some play until locked into place. Although short bars 206 of equal length are illustrated, it will become apparent that the system is quite flexible, and may take advantage of bars of different or adjustable lengths and profiles. An aperture such as 314 may be provided to enable a tool to move the connectors into a desired position, or remove the body 204 from the screw 302, as appropriate.

Figure 3J:
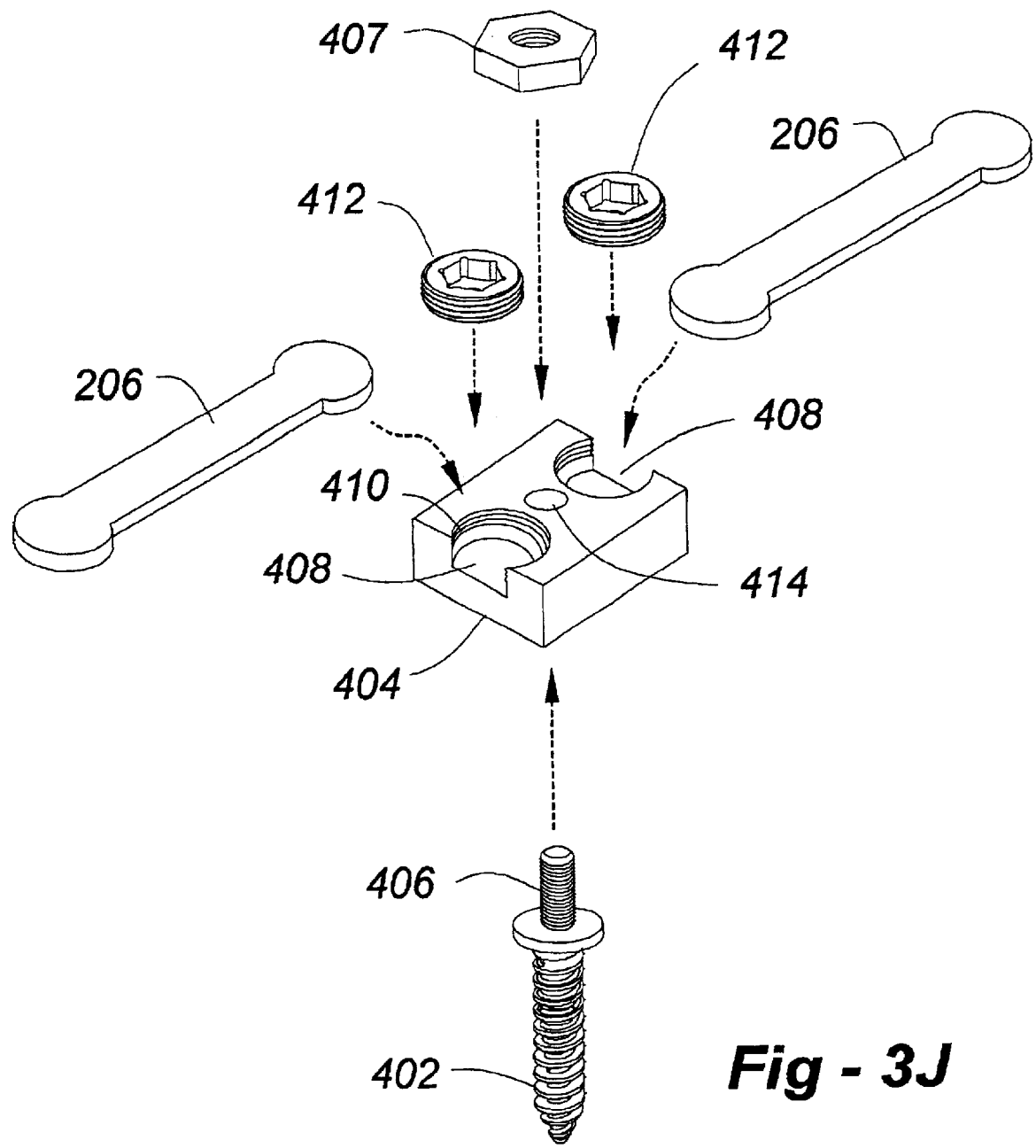
FIG. 3J illustrates an embodiment of the invention similar to that depicted in FIG. 3I, but wherein the pedicle screw includes a threaded end as opposed to a ball-end-socket type of connection.

FIG. 3J illustrates an alternative embodiment of the invention, wherein the swivel joint between the pedicle screw and connector body is replaced with a screw 402 having a threaded end 406. The threaded end 406 now protrudes through a larger hole 414 in the connector body 404, enabling a nut 407 or other suitable fastener to lock the body 404 onto the screw 402. Similar to the embodiment of FIG. 3A, however, link bars 206 fit into recesses 408 in the body 404, and set screws 412, which mate with threads 410, are similarly used to lock the link bars into place once a desired orientation is achieved.

Figure 3K:
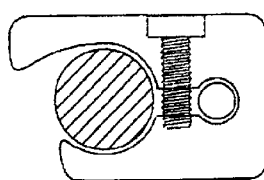
FIG. 3K is a side view of a preferred transverse connector according to the invention.
Figure 3M:
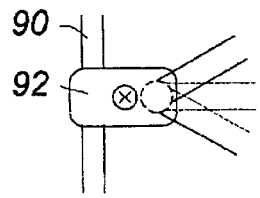
FIG. 3M is a top view of the transverse connector of FIG. 3K, illustrating multiple degrees of freedom made possible by the arrangement.
Figure 3L:
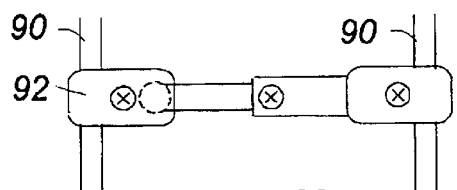
FIG. 3L is a top view of the transverse connector of FIG. 3K.
Figure 3N:
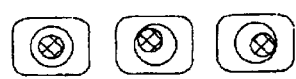
FIG. 3N depicts multiple views of the preferred transverse connector of FIG. 3K, showing various degrees of angulation.
Figure 3O:
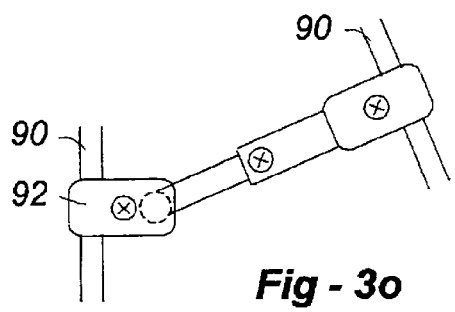
FIG. 3o illustrates the use of a ball joint which permits the preferred transverse connector to accommodate non-parallel rods.
Figure 3P:
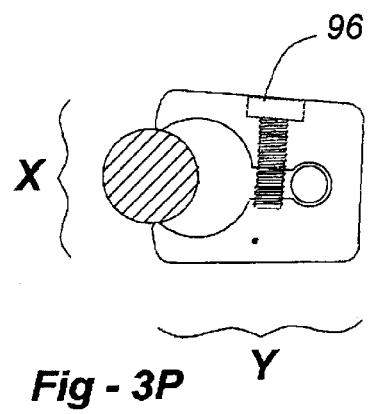
FIG. 3P is an end view of the preferred transverse connector used to illustrate the desirability of reduced dimensions.

FIG. 3K is a side view of a preferred transverse connector according to the invention. FIG. 3L is a top view of the transverse connector of FIG. 3K, showing how bodies 92 clamp onto rods 90. FIG. 3M is a top view of the transverse connector of FIG. 3K, illustrating multiple degrees of freedom made possible by the arrangement. FIG. 3N depicts multiple views of the preferred transverse connector of FIG. 3K, showing various degrees of angulation. FIG. 3o illustrates the use of a ball joint which permits the preferred transverse connector to accommodate non-parallel rods. FIG. 3P is an end view of the preferred transverse connector used to illustrate the desirability of reduced dimensions. In particular, dimensions X and Y are both reduced according to the invention, and fastener 96 is not engaged until the two halves of the unit are brought into close proximity.

Figure 4A:
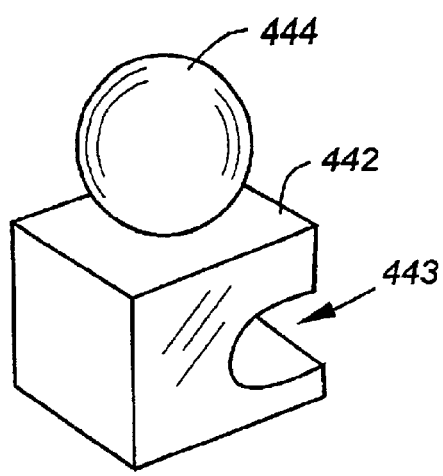
FIG. 4A illustrates a sublaminar hook according to the invention having a ball-shaped connector.
Figure 4B:
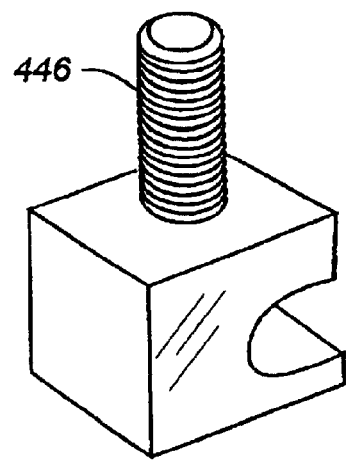
FIG. 4B illustrates a sublaminar hook according to the invention having a threaded connector.
Figure 4C:
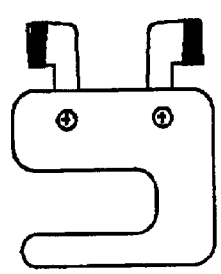
FIG. 4C illustrates a sublaminar hook embodiment of the invention featuring two opposing spherical joints.
Figure 4D:
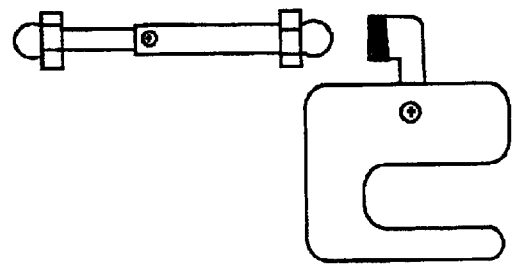
FIG. 4D illustrates a sublaminar hook embodiment of the invention featuring a single spherical joint.

FIGS. 4A and 4B are drawings of improved sublaminar hooks constructed according to the invention. Broadly, these devices include bodies such as 442 having a recess such as 443 configured for engagement with sublamina, but in contrast to existing devices, either a hemispherical connector 444 or threaded connector 446 are provided on the body to engage with the inventive link connectors discussed, for example, with reference to FIGS. 3A and 3B. FIG. 4C illustrates a sublaminar hook embodiment of the invention featuring two opposing spherical joints. FIG. 4D illustrates a sublaminar hook embodiment of the invention featuring a single spherical joint.

Figure 5A:
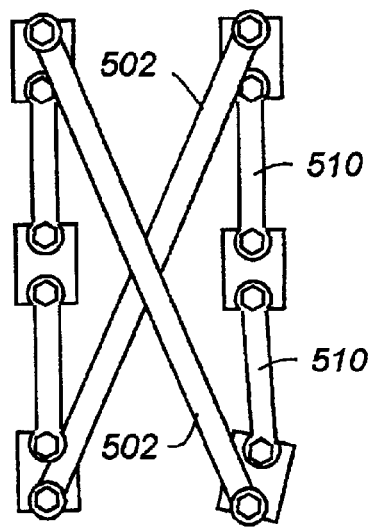
FIG. 5A illustrates one use of cross-links according to the invention.
Figure 5B:
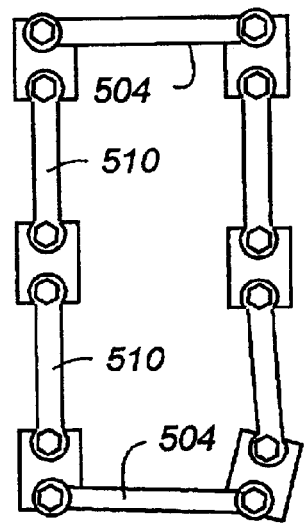
FIG. 5B illustrates an alternative cross-link configuration according to the invention.

FIGS. 5A and 5B illustrate, respectively, two ways in which connectors according to the invention may be cross-linked, with the understanding that additional variations are certainly possible. In FIG. 5A, longer link members 502 are used to link the sides of the connector in criss-cross fashion, whereas, in FIG. 5B, shorter link members 504 are used in a manner transverse to those oriented from foot-to-head along the spine. Note also that the plate and rod connectors may be used separately or together; that is while it may be advantageous to use plates at 502 and 504 for transverse interconnection, spherical joints may be preferred longitudinally along the spine, as in locations 510.

Figure 6A:
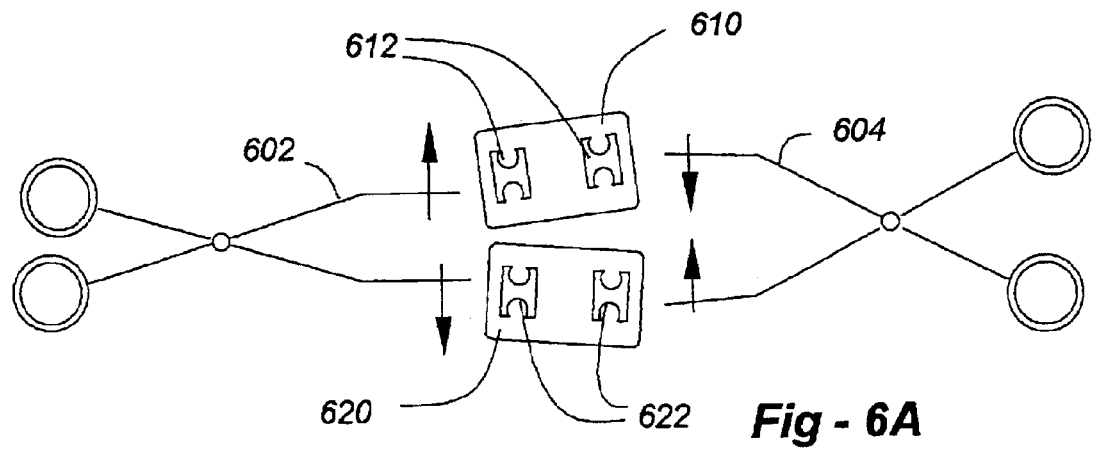
FIG. 6A shows the use of clamps as part of a first step to realign vertebrae for use with at least one embodiment of the invention.
Figure 6B:
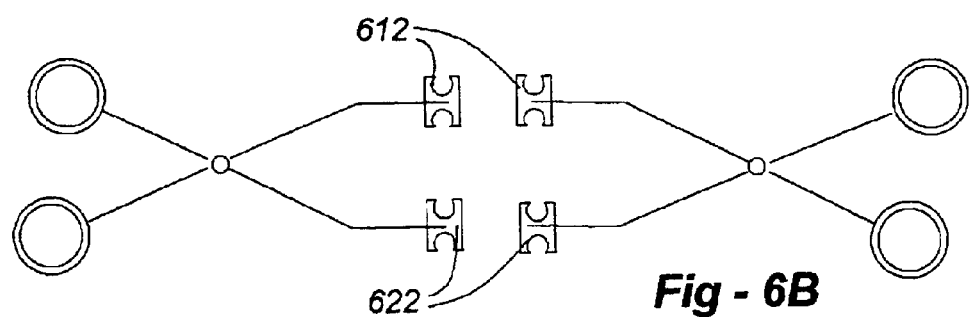
FIG. 6B shows the vertebrae in alignment using the clamps of FIG. 6A.
Figure 6C:
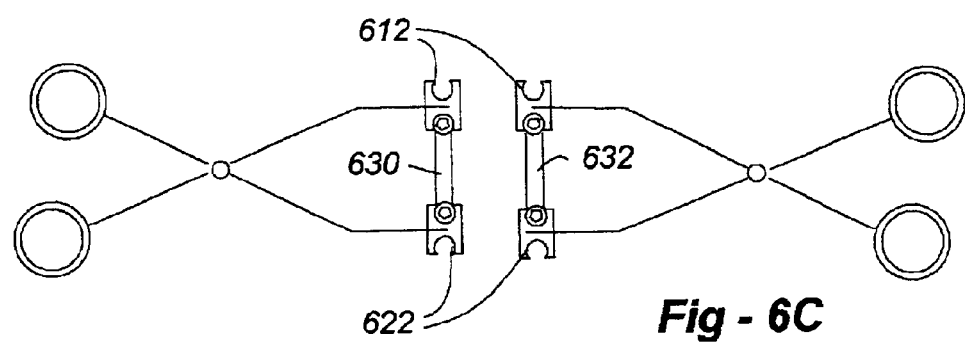
FIG. 6C shows the installation of linking rods to align the vertebrae, enabling the clamps to be removed.

FIGS. 6A–6C illustrate the way in which instrumentation may be used to obtain a desired degree of vertebral correction, at which time the link members may be added to maintain the structure in correct alignment. In FIG. 6A, vertebrae 610 and 620 are mal-aligned, and instruments 602 and 604 are used to adjust them into a proper orientation. Generally speaking, instrument 602 is used to urge apart the connectors shown in the left part of the drawing, where the vertebrae are too close to one another, whereas instrument 604 is used to pull the vertebrae together.

FIG. 6B is a drawing which shows a desired orientation of the connectors 612 and 622, without the vertebrae being shown, and FIG. 6C illustrates how, having achieved a desired final position, link members 630 and 632 are tightened onto the connectors 612 and 622, at which time the instruments may be removed. This process is more or less repeated, on adjacent vertebral levels, until an overall desired level of alignment is achieved. Given the ease with which the link members and the connectors themselves may be readjusted, the surgeon may readily go back over areas in need of further refinement, as appropriate.

Figure 7D:
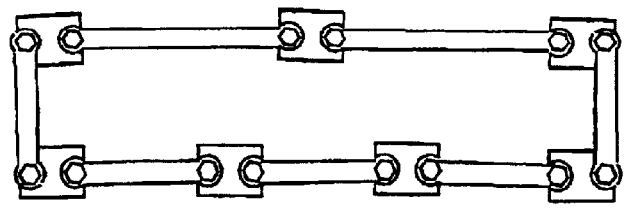
FIG. 7D illustrates a completed rod-and-connector structure to restore frontal alignment.
Figure 7C:
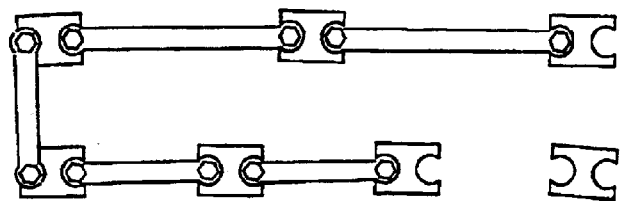
FIG. 7C illustrates an intermediate rod installation.
Figure 7B:
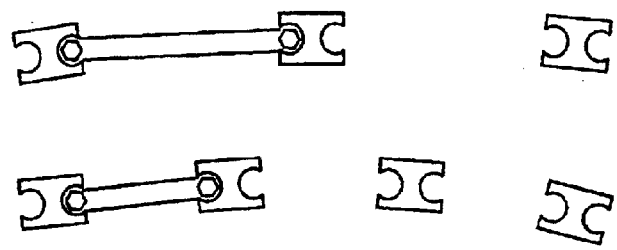
FIG. 7B illustrates an initial application of rods to restore frontal alignment.
Figure 7A:
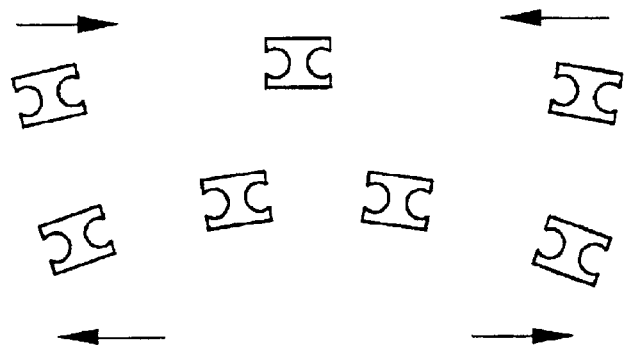
FIG. 7A shows a first step associated with restoring frontal alignment according to the invention.

This process is shown in FIGS. 7A through 7D with respect to the restoration of a frontal alignment. In FIG. 7A the spine is curved as shown, with seven connectors being positioned by the surgeon on the various vertebrae to begin the correction process. In FIG. 7B, the connectors shown upwardly in the drawing are first brought into alignment, and in FIG. 7C, cross-links and additional link members have been added further down the spine. In FIG. 7D, all of the connectors are linked up, with fine adjustments being made in three dimensions, as necessary, for a desired degree of correction. Again, although two rod-receiving position are shown with respect to each body, use of the bodies and link members of FIGS. 3D through 3H would proceed in like fashion.

In restoring the frontal alignment just described, the manual instruments of the type shown in FIGS. 6A–6C would be appropriate, though they are not shown in FIGS. 7A–7C. To restore sagittal alignment, a different form of instrument is preferred, to raise and lower connectors as opposed to pushing and spreading. Instruments according to the invention for this purpose are shown in FIGS. 8A–8C. In FIG. 8A, a tool 802 is inserted into connectors 804 and 806, and in FIG. 8B, the connectors are brought into sagittal alignment. In FIG. 8C, a link member 810 is fastened to the connectors, and the tool 802 removed.

In all of the rod-receiving bodies described herein, small apertures or slots may be provided to receive a tool for corrective positioning and, with the aid of a specialized instrument such as 900 depicted in FIG. 9. Using such a tool, the body may be removed from the ball-tipped hooks or pedicle screws previously described, as appropriate. Such a tool would preferably include side portions 902 and a central pin 906 which may be forced down through the opening 314 by handle 910, thereby applying force between the body and hook or screw to remove the connector for repositioning or removal.

FIG. 10 is a side-view drawing of an alternative connector system according to the invention, wherein angled, preferably reinforced components 1002 are fastened to pedicle screws 1004. The members 1002 provide one or more holes, better seen in FIGS. 11 and 12, to which link members such as 1110 may be fastened. Note that the pieces 1102 would preferably be provided in various heights and sizes better accommodate a given patient physiology.

FIG. 11A is a drawing which shows one way in which the connectors introduced with respect to FIG. 10 would be used in practice. Six connectors such as 1102 are shown, each having four holes to receive link bars. With this many fastening points, multiple reinforcements may be used. In particular, both lateral and diagonal cross members are readily accommodated. Moreover, as shown in FIG. 11B, the holes may be used for devices other than the link members. For example, cables 1110 may be used where appropriate, and in some cases may be wrapped around the lamina (sublaminally) as depicted with numerical reference 1112.

Rigid link members and cables may also be used with the alternative connector 1202 of FIG. 12A, which includes holes 1204 on one side for link bars and additional holes 1206 on the other side for cables. FIG. 12B shows the alternative connector of FIG. 12A in use, with a combination of cables 1216 and rigid link members 1214 (shown as lines) being used to establish a stable, cross-coupled structure.

Figure 14:
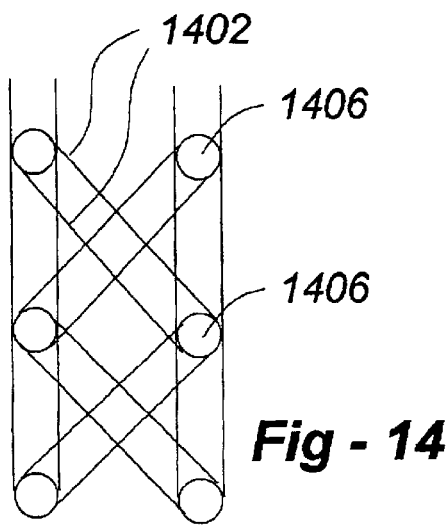
FIG. 14 shows diagonal connectors for use with existing rod or plate systems, but with attachment made relative to the pedicle screws as opposed to the linking members.

FIG. 13 illustrates an alternative arrangement according to the invention, wherein cables 1302 are applied to an existing rod/plate system to impart further structural integrity. Four diagonally oriented cable paths are used, though more or fewer may be employed, depending upon the needs of the patient. In contrast to interconnection of the cables to the rods themselves, as shown in FIG. 13, cables 1402 may be applied to the screws 1406 binding the rods to the vertebrae, as shown in FIG. 14.

Figure 15A:
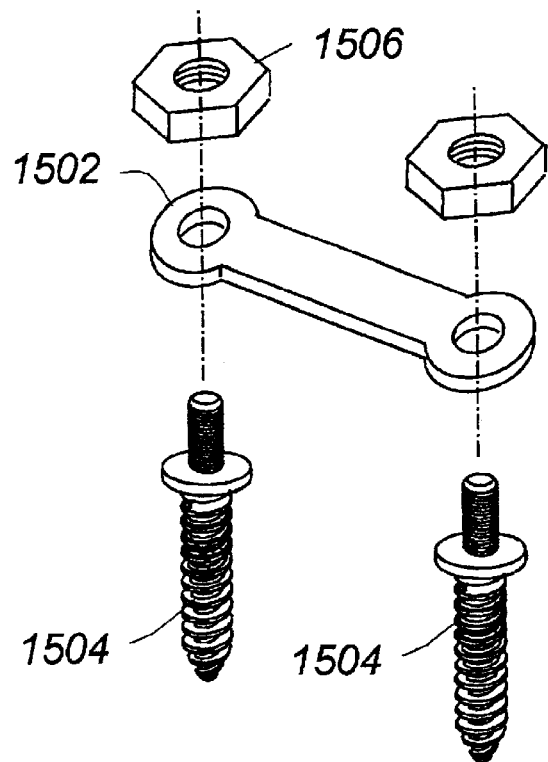
FIG. 15A illustrates an alternative embodiment wherein struts are stacked over one another onto pedicle screws.
Figure 15B:
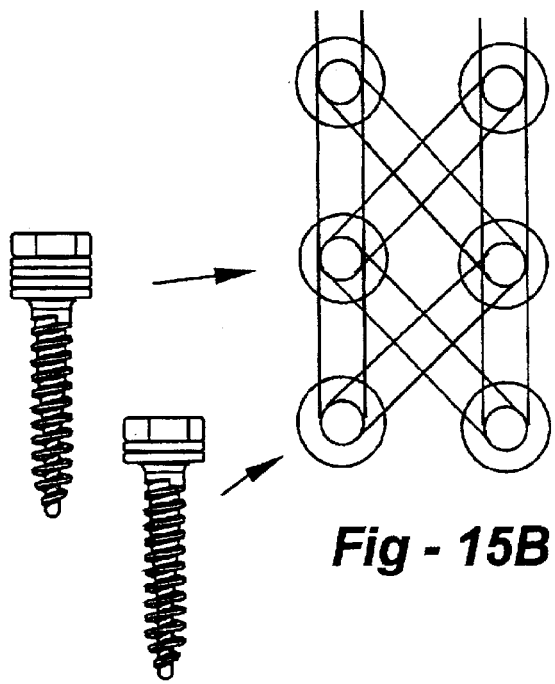
FIG. 15B illustrates the use of cross-link member in conjunction with the embodiment of FIG. 15A.
Figure 16:
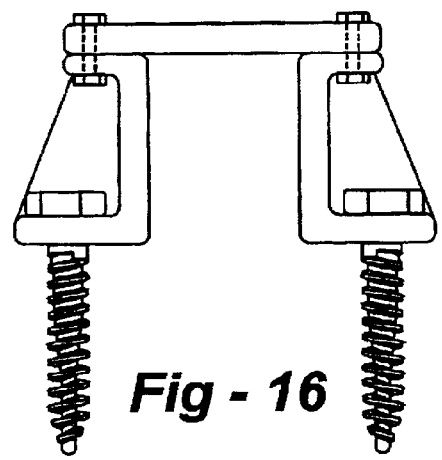
FIG. 16 is a side-view drawing of yet a further alternative connector according to the invention wherein more space is provided to tighten and loosen associated pedicle screws.

FIGS. 15A and 15B illustrate yet a further, different embodiment of the invention, wherein a rigid link bar 1502 is attached to pedicle screws 1504 using nuts 1506 or other appropriate fasteners. With a sufficiently long exposed threaded end, multiple link members may be used in conjunction with each pedicle screw in a stacking arrangement, thereby allowing for a criss-crossed structural assembly, as shown in FIG. 15B.

As opposed to rigid link members of a fixed length, the invention also anticipates the use of telescoping members, including the type shown generally at 1700 in FIG. 17. Each end of such a device would include a flat plate, ball, or fastener such as 1702 and 1703 appropriate to one of the connector systems disclosed herein, but with the length being variable in telescoping or sliding fashion. Preferably, one or more setscrews 1704 would be used to lock the member in accordance with a desired length at any time, including in the midst of an adjustment procedure. Any cross-sectional geometry may be used, so long as a telescoping action is provided. In particular, whereas a cylindrical geometry may allow for twisting as well as extension prior to locking in place, non-circular cross-sections may be used to permit extension/contraction without twisting, as desired.

FIGS. 18A–18C illustrate a sublaminar connector 1800 according to the invention, having discs 1802, preferably which swivel, to which the telescoping rods of the type shown in FIG. 17 may be adjustably attached. FIG. 18A presents one view of such a device, showing a lower hook 1820 adapted for sublaminar engagement. FIG. 18B shows a top-view of the device, and FIG. 18C is a cross-sectional view, with arrows used to indicate the preferred swivel action.

FIG. 19 is a drawing of a further alternative device 1900 having connectors 1902, which also preferably swivel, but include a pedicle screw 1904 for fixation as opposed to a sublaminar engaging portion, as shown in FIGS. 18A–18C. Note that although the body of the device 1900 is depicted integrally with the pedicle screw 1904, the body may be connected to lower screw portion through a connector shown with broken lines at 1910.

Installation and operation of the devices of FIGS. 18 and 19 are shown in FIGS. 20 and 21, incorporating the sublaminar device of FIG. 18, pedicle screw unit of FIG. 19, and threaded rod of FIG. 23. FIG. 20 is a lateral view of an assembly utilizing these devices, whereas FIG. 21 is a posterior-anterior view.

A preferred way in which the telescoping rods and fixation devices discussed above will now be described to align a problem with curvature. In FIG. 22A, a telescoping rod 2202 is sized relative to a pair of connectors 2204 and 2204' to be aligned, with fasteners 2206 with nuts 2208 being provided for tightening purposes. FIG. 22B shows the telescoping rod 2202 attached to the connectors 2204, with the arrows being indicative of the way in which the segments of the rod are moved to displace the connectors prior to tightening. FIG. 22C shows how the segments of the rod are locked onto the connectors in an extended position, enabling the vertebrae to be distracted and aligned. It will be clear to one of skill that, as opposed to extension, the segments of the rod 2202 may be brought together, as the case may be, to provide a desired amount of compression.

FIG. 23 is a side-view drawing of a preferred cross-connector 2300 according to the invention, which may be used in conjunction, or in place of, the extensible rods just described. The assembly includes a threaded rod 2300, onto which the preferably swiveling attachment mechanisms 2304, 2304' of the connectors are journaled. On either side of the connectors, washers such as 2306, 2306' and nuts such as 2308, 2308' are also preferably used for a precise, yet stable alignment when tightening.

Although the telescoping and threaded rods have thus far been depicted as straight, they may be curved or bent for different situations. In the case of the telescoping rod, both ends may additionally be adjustable, as shown in FIG. 24. The connector bodies may be attached to the rods such as 2500 in various ways, including the use of a set screw 2502 or other fastener, as shown in the cross-section of FIG. 25.

Figure 26A:
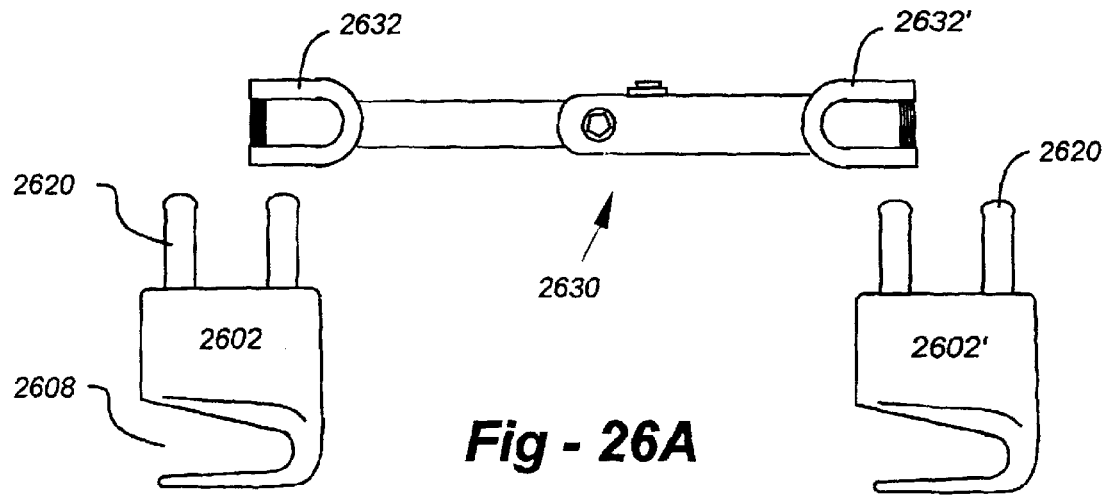
FIG. 26A illustrates the use of a further alternative embodiment of the invention featuring a telescoping rod that engages with hooks having one or more posts.
Figure 26B:
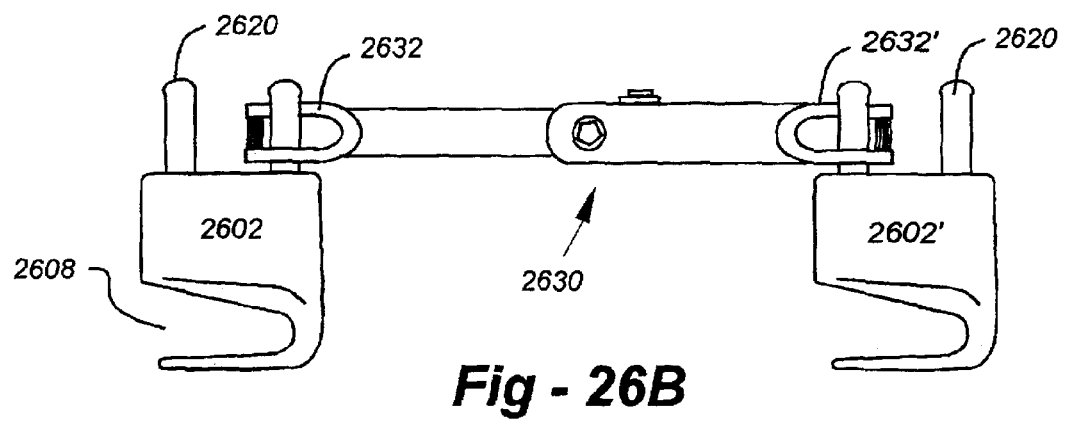
FIG. 26B shows the rod of FIG. 26A being rotated to achieve a desired level of alignment.
Figure 26C:
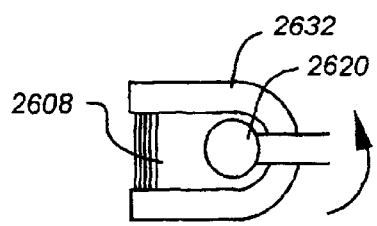
FIG. 26C is a close-up view of the rotation procedure.

FIGS. 26A–26C illustrate an alternative interconnection mechanism which may be used in conjunction with, or in place of, the circular swivel-type connectors described above. In this case, the connectors bodies 2602, 2602', which may feature pedicle screws or sublaminar hooks 2608, as shown, would include one or more posts such as 2620 extending therefrom, onto which elongated elements 2630 having closed-fork ends such as 2632, 2632' would be journaled, adjusted, then tightened for a desired level of alignment. Although a telescoping rod is shown, threaded arrangements should also be apparent to those of skill, as described above with reference to the swivel-type arrangements.

FIG. 26A shows a telescoping version of this embodiment prior to placement onto bodies 2602, 2602'. FIG. 26B shows the fork-shaped ends 2632, 2632' being placed onto the posts, and FIG. 26C shows the way in which the ends are tightened onto the posts, preferably through the use of a set screw 2608 which applies pressure to the cylindrical portion of the hook to lock it into position. The setscrews are locked onto the connectors to avoid the frustration of inserting the setscrew into a small space on the hook itself. Using the arrangement of the invention, the setscrews may be tightened or loosened, but will not be removed from the connector and inadvertently lost. Preferably, the cylindrical projections from the hook or pedicle screw bodies have an enlargement at their ends to help prevent the connector from sliding off the hook once it is tightened in place.

Figure 27:
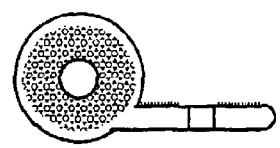
FIG. 27 is a drawing of an alternative connector according to invention providing the ability to vary angulation in two planes.
Figure 28:
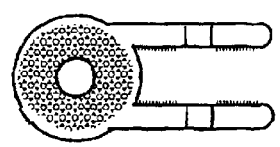
FIG. 28 is an alternative connector according to the invention which also affords multiples degrees of freedom.

FIG. 27 is a top-view drawing of an alternative connector adapted for use with any of the swivel-type embodiments described herein, the configuration permitting variable angulation in two additional planes. FIG. 28 is a further adaptation of the device of FIG. 28, also providing lockable angulation with multiple degrees of freedom.

Figure 29A:
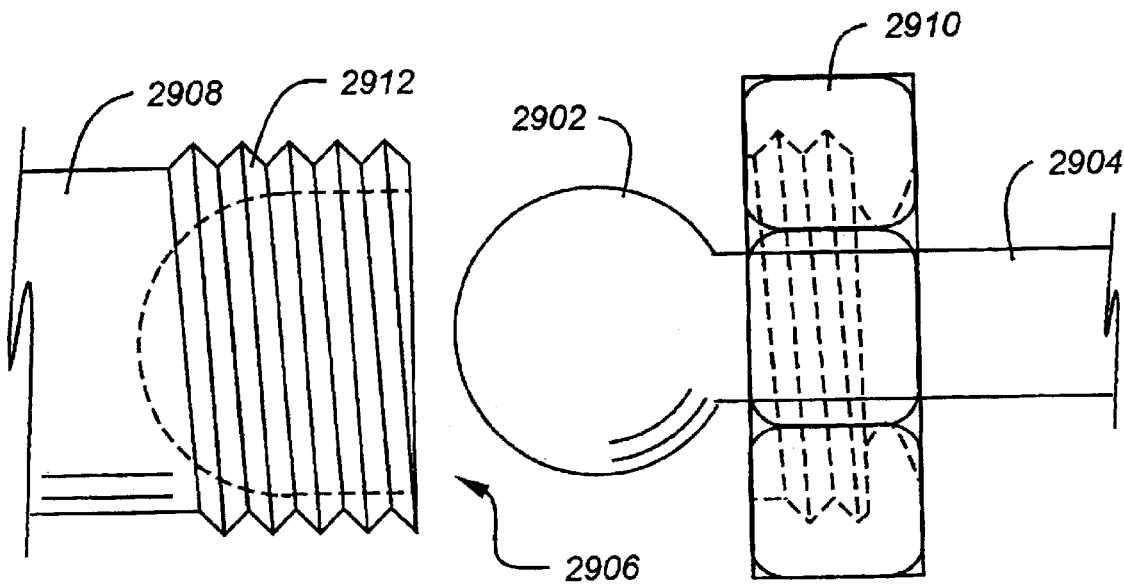
FIG. 29A is a drawing of an alternative connector according to the invention which uses a ball and socket held in position with a threaded fastener.
Figure 29B:
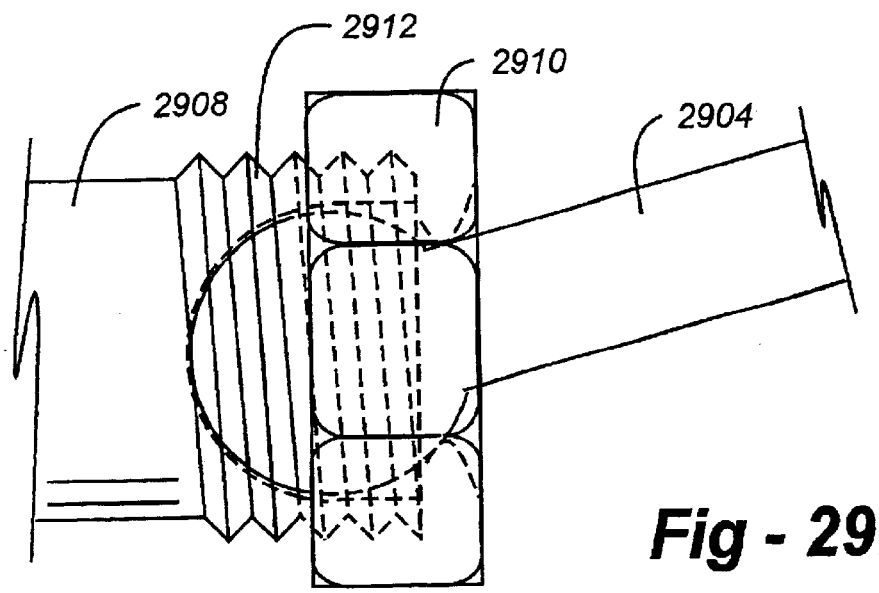
FIG. 29B shows the alternative connector of FIG. 29A locked into a desired orientation.

FIGS. 29A and 29B depict an alternative connector system according to the present invention. Broadly, the system uses a ball-shaped connector 2902 on a rod 2904 or other member, where the spherical end 2902 fits into a socket 2906 on member 2908. Journaled over the element 2904 is a threaded nut 2910 which engages with threads 2912 on element 2908, thereby locking the device into a desired orientation, as shown in FIG. 29B.

Figure 30A:
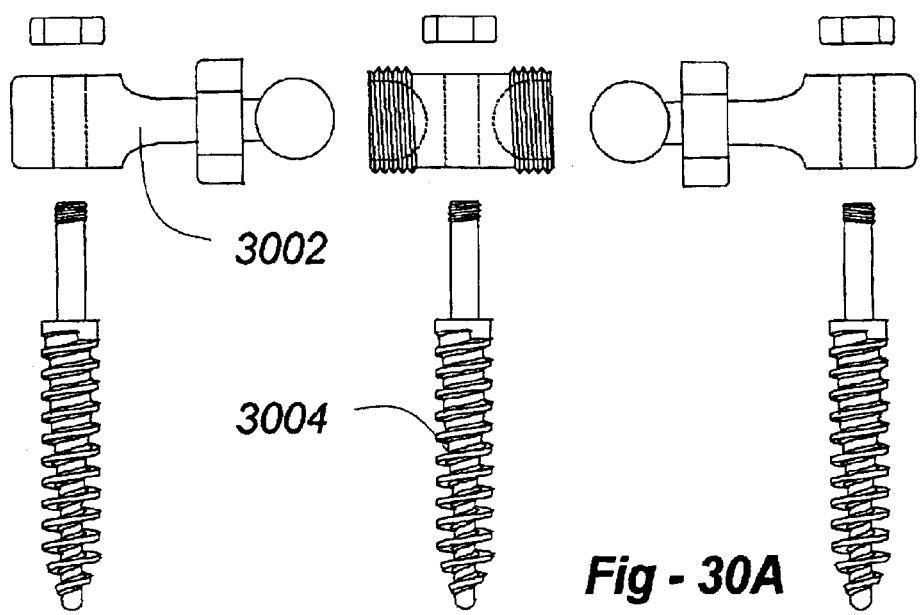
FIG. 30A is a drawing which shows an embodiment of the invention wherein a connector body and elongated element are integrally formed to achieve a low-profile interconnection scheme.
Figure 30B:
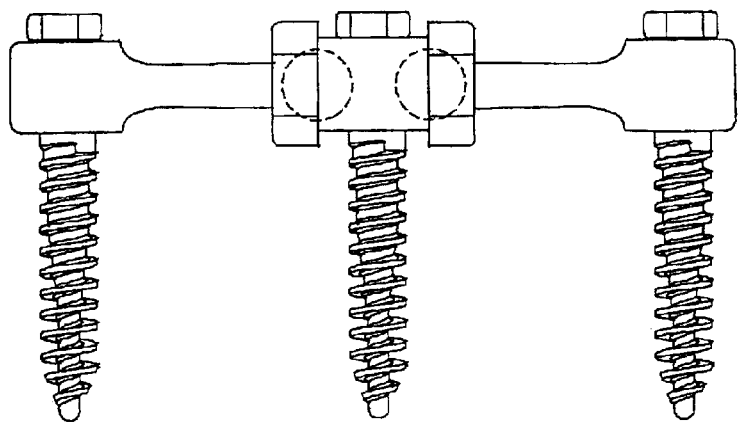
FIG. 30B shows the configuration of FIG. 30A in an assembled condition.
Figure 30C:
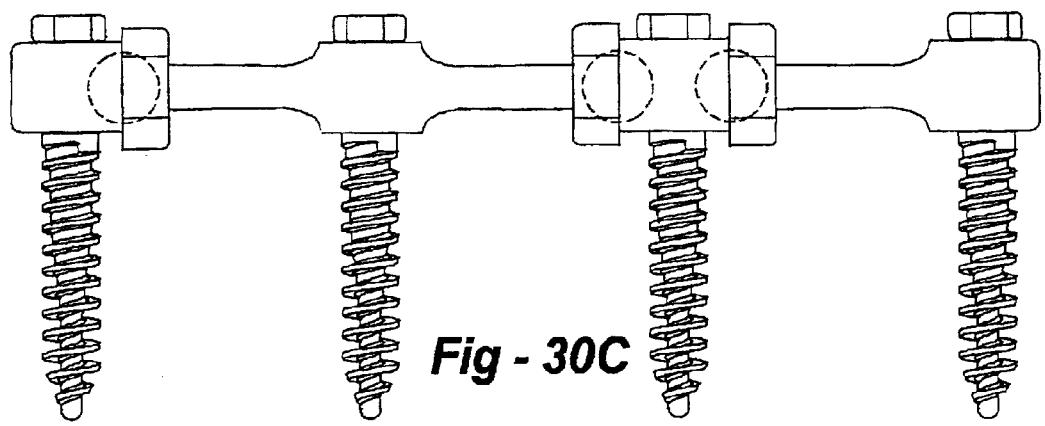
FIG. 30C shows the way in which connector bodies having multiple male and female connectors may be joined together in succession.

FIG. 30A is a drawing which shows an embodiment of the invention wherein a connector body and elongated element are integral, providing a low-profile solution particularly for shorter interconnections. Longitudinal member such as 3002 is incorporated into the connector to facilitate insertion into adjacent vertebrae. As such, the combined unit is inherently shorter. Also, note that the connector on the middle screw 3004 is attached to the pedicle screw through a threaded post. Once again, this shortens the unit, particularly in areas of the spine where the attachments to the vertebrae are farther apart and where more spinal deformity may be present. Multiple connectors may also be used to increase the allowed angulation between vertebrae, as shown in FIGS. 30B and 30C.

Figure 31C:
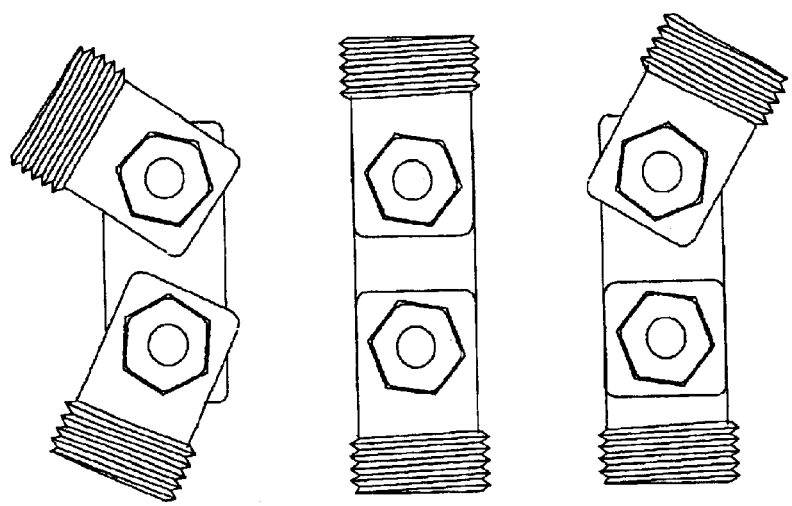
FIG. 31C is a series of top-down drawings illustrating the swiveling feature of the embodiments of FIGS. 31A and 31B.
Figure 31B:
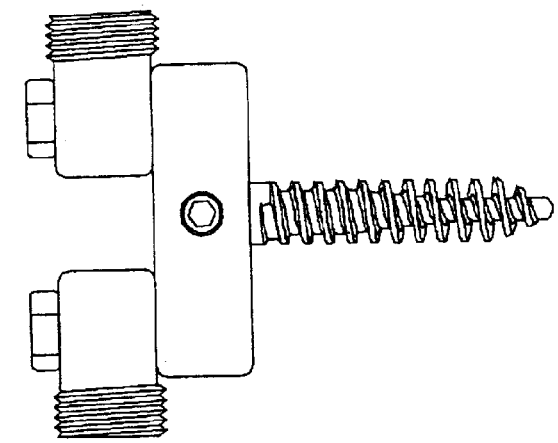
FIG. 31B shows the arrangement of FIG. 31A in an assembled condition.
Figure 31A:
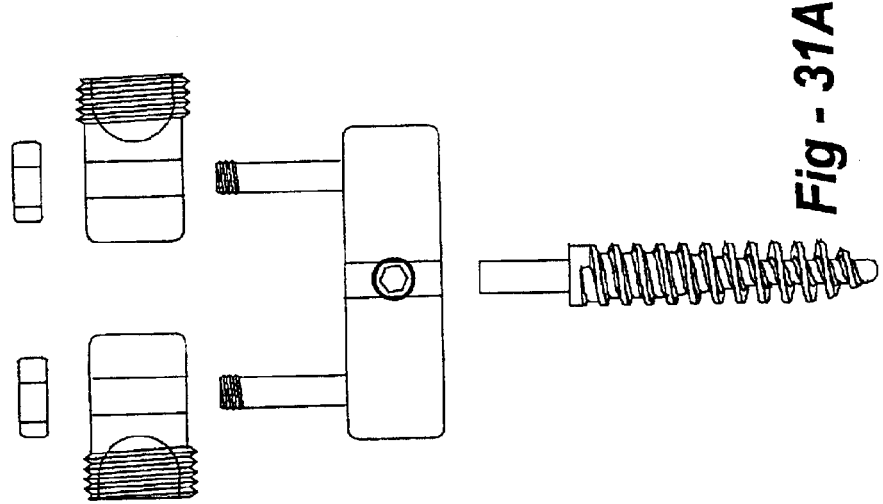
FIG. 31A is a drawing which shows a swiveling, socket-type connector according to the invention on a body attached to a pedicle screw.
Figure 32:
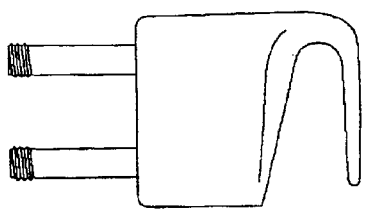
FIG. 32 is a drawing which shows a sublaminar hook having outward projections to receive swivel connectors.

FIG. 31A is a drawing which shows swiveling socket-type connectors on a body attached to a pedicle screw. FIG. 31B shows the arrangement of FIG. 31A in an assembled condition. FIG. 31C is a top view illustrating the swiveling feature of the embodiments of FIGS. 31A and 31B. Such swivel connectors may also be incorporated into a sublaminar hook configuration. Hooks and sublaminar attachments do not require the connector-connector feature, however, since devices of this type are slid into position. FIG. 32, for example, is a drawing which shows a sublaminar hook having outward projections to receive the swivel connectors.

Figure 33B:
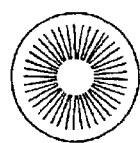
FIG. 33B is a top view of a screw connector according to the invention having a single post.
Figure 33E:
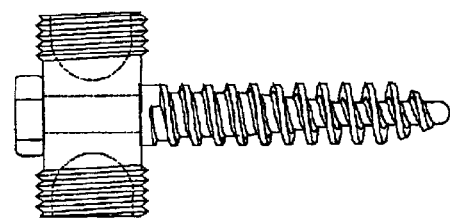
FIG. 33E shows how one or more manually adjustable fasteners may be added to help control rotation of a connector according to the invention.
Figure 33A:
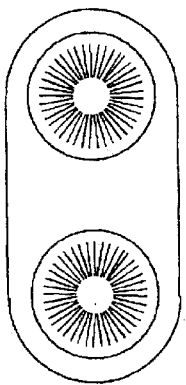
FIG. 33A is a drawing of a top-down view of a screw connector having two posts.
Figure 33D:
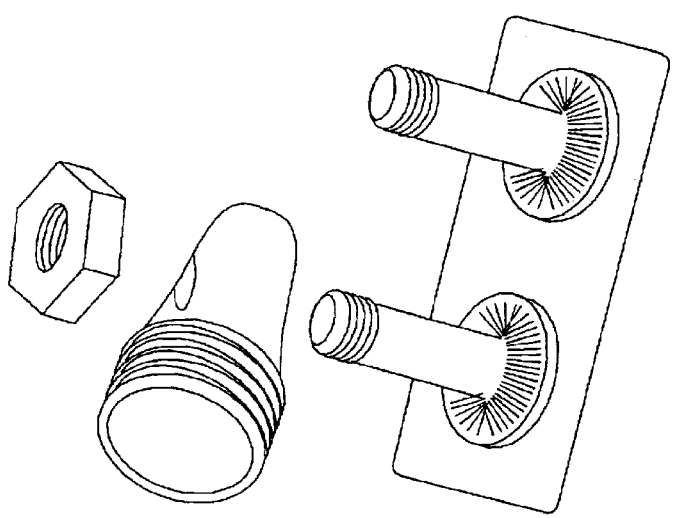
FIG. 33D is an oblique drawing which shows the use of frictional surfaces to lock in the swivel action upon achieving a desired orientation.
Figure 33C:
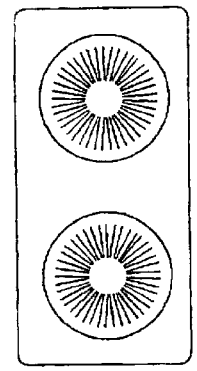
FIG. 33C is a top view of a single hook connector.

FIG. 33A is a drawing of a top view of a screw connector having two posts. FIG. 33B is a top view of a screw connector according to the invention having a single post. FIG. 33C is a top view of a hook connector. FIG. 33D is an oblique drawing which shows a preferred use of frictional surfaces to lock in the swivel action upon achieving a desired orientation. The friction surface may also be incorporated between the connectors and the screws or hooks. FIG. 33E shows how a set screw (or screws) may be added to help control rotation of a connector according to the invention.

Figure 34A:
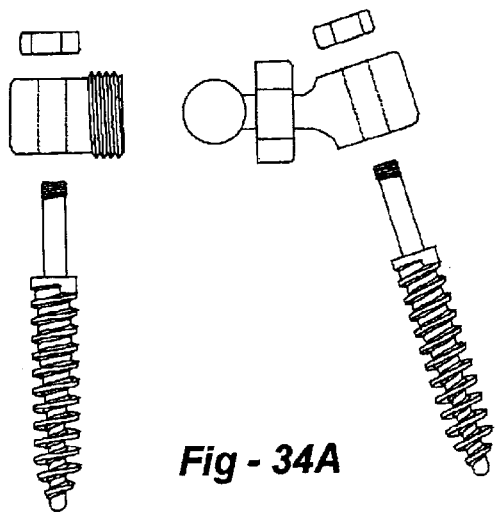
FIG. 34A shows how a combined longitudinal member and connector may have different lengths and angles to address different alignment situations.
Figure 34B:
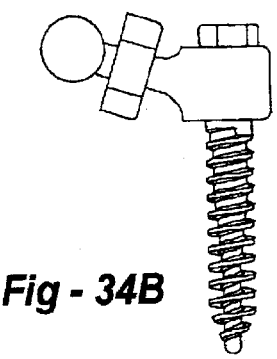
FIG. 34B illustrates an assembled version of an angled unit.

The combined longitudinal member-connector unit may feature a variety of lengths for the longitudinal members, as well as angles between the longitudinal member and connector. FIG. 34A, for example, shows how a combined longitudinal member and connector may have a particular length and angle to address a particular situation. FIG. 34B illustrates an assembled version of the angled unit of FIG. 34A.

Figure 35:
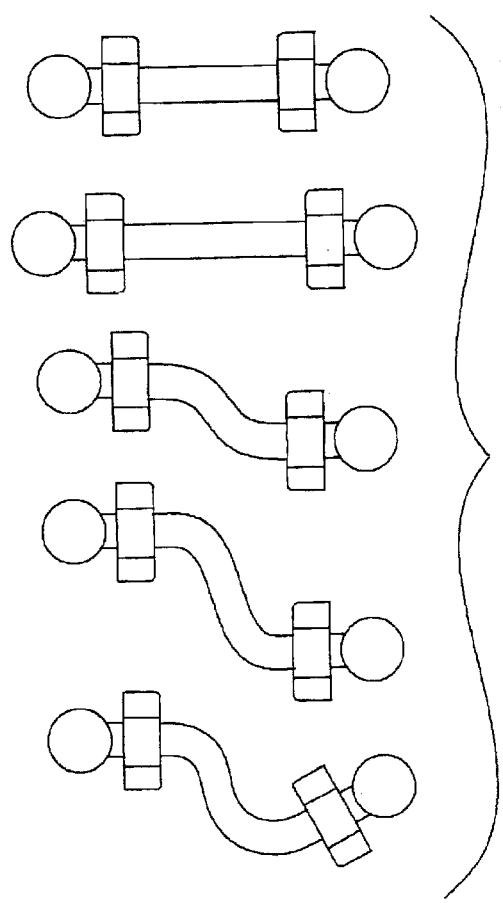
FIG. 35 is a series of drawings which show a variety of longitudinal members in straight and curved configurations.

FIG. 35 is a series of drawings which show a variety of longitudinal members in straight and curved configurations. The longitudinal members shown in FIG. 35 are preferably pre-fabricated in various sizes and shapes with the nuts attached. They are used when the space between the attachment sites on the vertebrae are close together. Depending upon material choice, they may be further bent by the surgeon at the time of surgery as necessary. When the space between the vertebrae attachment sites is larger than the telescoping longitudinal member, a turnbuckle-like longitudinal member would preferably be used. It will be appreciated that these and other ball-ended configuration may incorporate the cap configurations of FIGS. 3G.

Figure 36A:
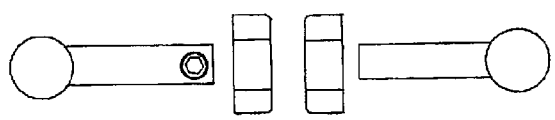
FIG. 36A shows how a telescoping member may be assembled through a pair of nuts, then joined.
Figure 36B:
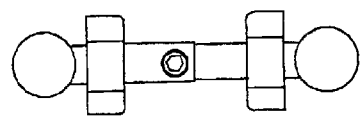
FIG. 36B shows a joined assembled version of the assembly of FIG. 36A.

The telescoping/tumbuckle members with nuts could also be assembled by the surgeon. For example, FIG. 36A shows how a telescoping member may be assembled through a pair of nuts then joined. FIG. 36B shows a joined assembled version of the assembly of FIG. 36A.

Figure 39:
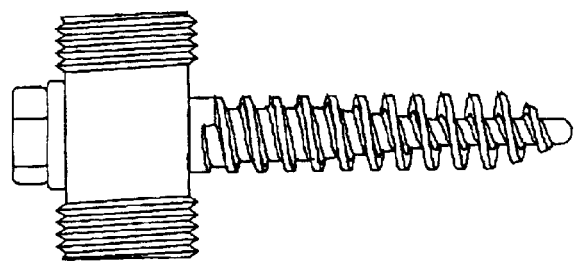
FIG. 39 is a side view of a connector according to the invention including a cross link.
Figure 38:
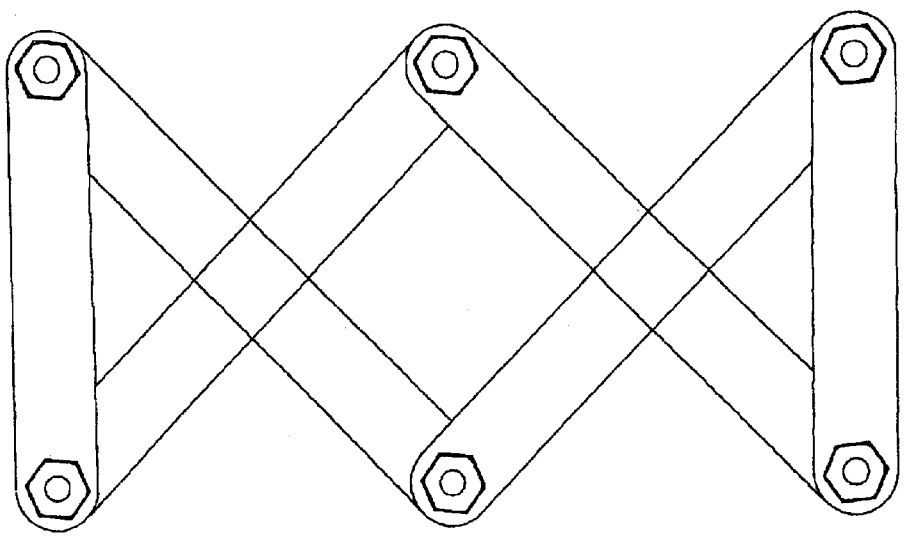
FIG. 38 illustrates the overlapping of rigid link plates at different vertebral levels.
Figure 37:
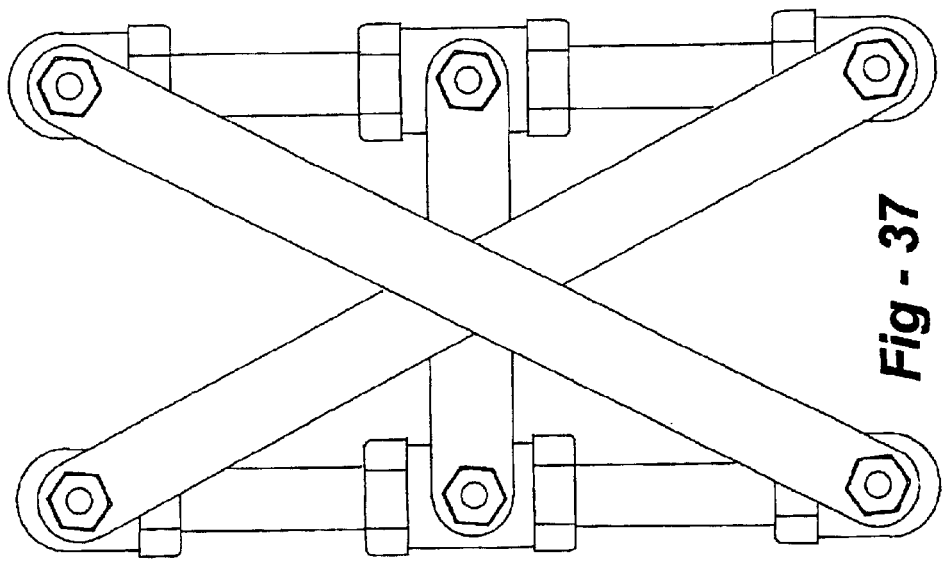
FIG. 37 illustrates the combined use of ball-and-socket connectors and rigid link plates.

The cross links may also be attached to the top of the central posts in many different configurations. FIG. 37 illustrates a plate-like embodiment of the cross-link. This embodiment shows only one cross-link end per connector. For more rigidity, the cross-links could be stacked. For example, FIG. 38 shows an embodiment with two cross-link ends per connector. The longitudinal members and connectors are not drawn in order to better illustrate cross-links, which are preferably thinner than the rigid longitudinal members in FIGS. 13 an 15. FIG. 39 is a side view of a connector including a cross-link.

This section of the description provides details of various connector configurations according to the invention, including designs particularly suited to different vertebral levels. In the accompanying drawings, the central connector bodies are threaded at the ends where engage with the longitudinal members. As discussed elsewhere herein, the central connectors may be threaded on either end, though the connectors at the end of a construct are preferably threaded on one end only. The central portion of the connector may include a flat surface, or may be square or rectangular to accommodate a wrench to stabilize the connector while tightening the nut and facilitate attachment to pedicle screw. The central portion of the connector may further include a pedicle hole to attach the connector to a pedicle screw. A friction surface may be provided between the connector (interior surface) and the pedicle screw superior surface.

FIGS. 40A–40F provide different views of a central lumbar connector according to the invention. In the lumbar region in particular, the connectors should be as short as possible. The pedicle screws may be 3 cm apart or closer. In this and in other embodiments, a friction surface may be provided between the rod ends and the connector seat. The connectors should be as small as possible in every dimension, since prominent hardware could cause the patient to experience pain.

FIGS. 41A–41G depict different views of a connector adapted to the cephalad end. As shown in FIGS. 41B and 41G, in particular, such connectors may have a special shape to avoid impingement on the first mobile facet joint of the spine. This is perhaps better visualized in FIGS. 58A and 58B. Note that if the inferior surface has a friction surface left and right units may be provided. Without a friction surface, however, the connector may be turned over for the other side. A special wrench (not shown) may also be provided to hold the connector while tightening the nut. The wrench could be the female version of the non-threaded portion of the connector attached to a handle.

The caudal end may use same connector as used in cephalad end. A reduced profile is not necessary, and the connector is similar in every other way to the cephalad connector. These connectors may also be used in other positions in patients with spinal deformities. Two connectors will preferably be used per pedicle screw or hook. The portion of the connector that attaches the hook or screw should be as small as possible to allow the connector to rotate. The connector should be as strong as possible to prevent fatigue fracture. If the connector is strong enough, it could also be used in the lumbar spine rather than the end connectors described above. This arrangement could reduce manufacturing costs by using a single type of end connector.

Figure 43A:
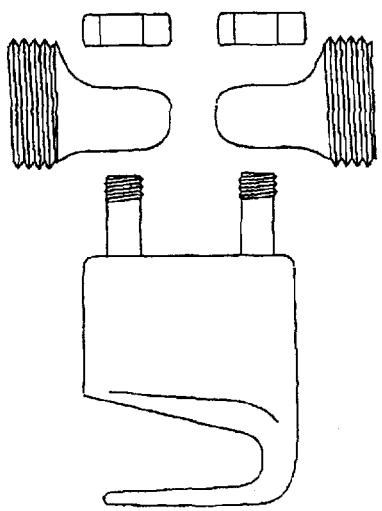
FIGS. 43A and 43B show an exploded and assembled views of sublaminar hooks with thoracic connectors attached thereto.
Figure 43B:
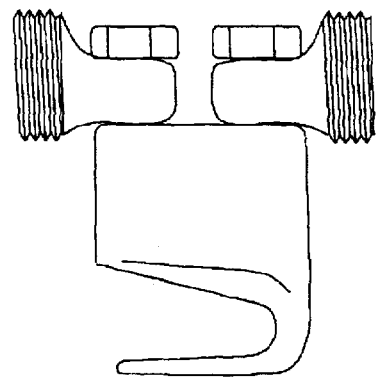
Figure 44A:
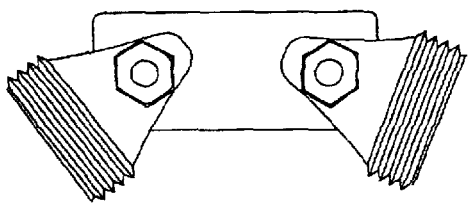
FIGS. 44A–44C are top views showing swiveling before and after locking into a straightened configuration.
Figure 44B:
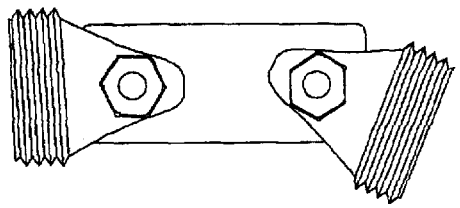
Figure 44C:
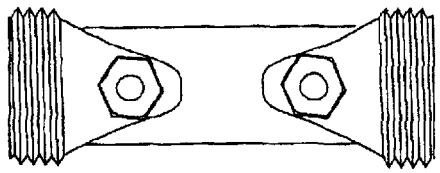

FIGS. 42A–42E show different views of a thoracic connector according to the invention. FIGS. 43A and 43B show an exploded and assembled views of sublaminar hooks with thoracic connectors attached thereto. FIGS. 44A–44C are top views showing swiveling before and after locking into a straightened configuration. The connectors rotate until tightening to allow for spinal deformity. They can be loosened and retightened to provide a desired level of correction.

Figure 45:
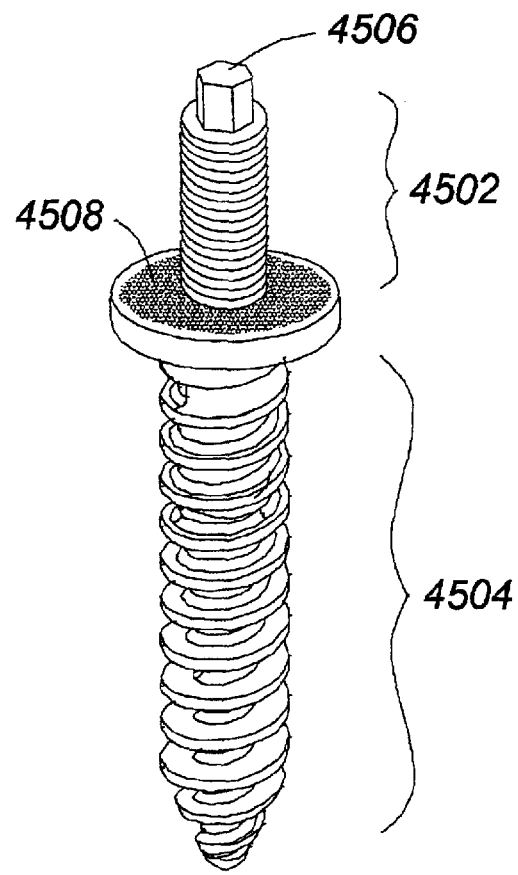
FIG. 45 is a drawing of a pedicle screw used to discuss different sizes and diameters.

FIG. 45 is a drawing of a pedicle screw used to discuss different sizes and diameters according to the invention. In the preferred embodiments, the pedicle screws feature a tapered minor diameter. Most screws break at the connection to the rod, since the bone near the tip of the screw is cancellous, whereas bone near the connector end is cortical. The deeper thread near the tip and constant major diameter for most of the screw serves to enhance pull-out strength. However, a relatively blunt tips are preferred to avoid vascular injury if the screw tip extends through the vertebra.

Generally a tap is used to provide a pathway for the screw. The bone is soft and some surgeons avoid the tapping step. Often a surgeon uses a tap for a 5.5 mm screw but insets a 6.5 mm screw.

Figures 46, 47, 48:
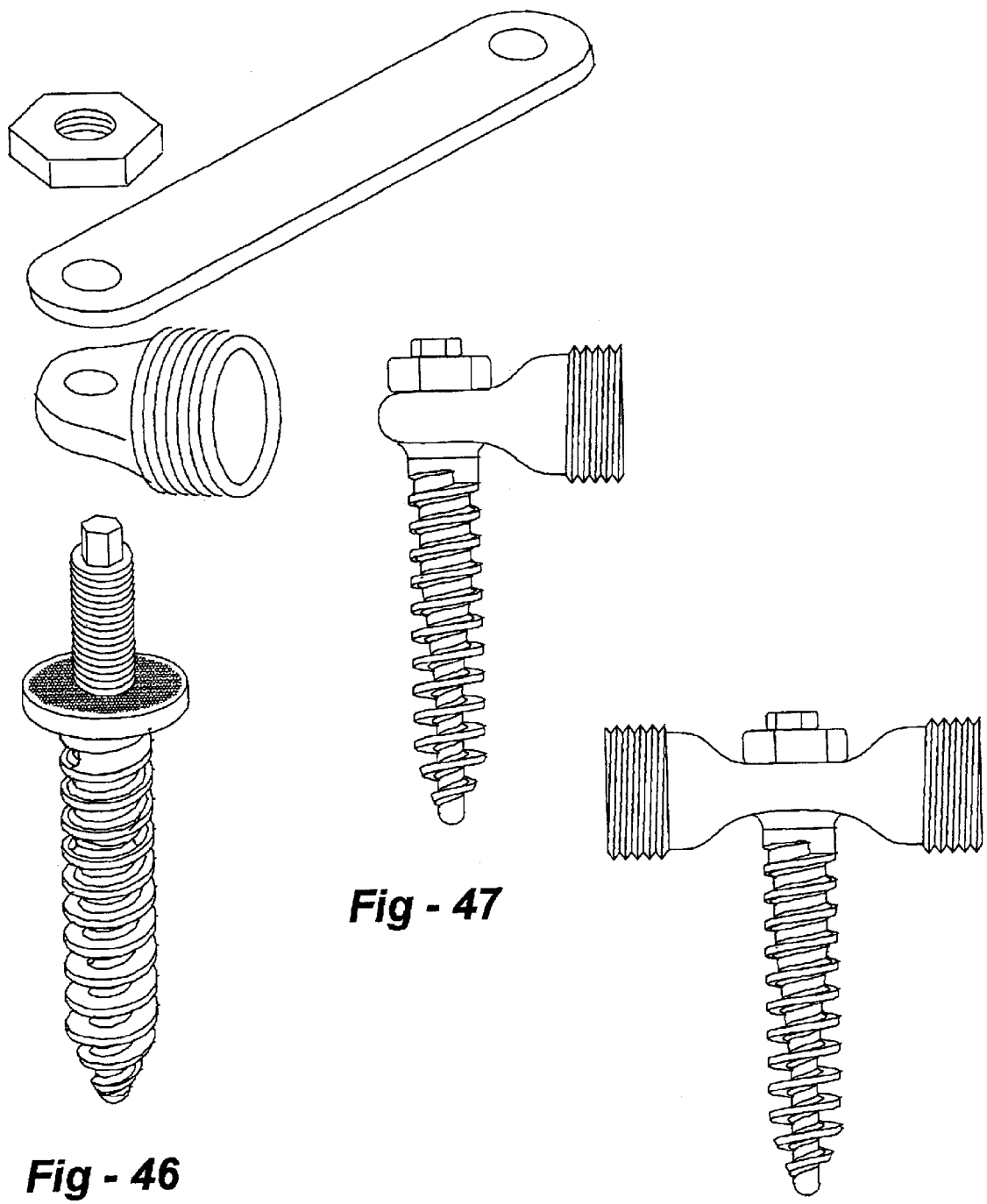
FIG. 46 is a perspective view of the pedicle screw of FIG. 45 including a ball connector and link bar.
FIG. 47 is a drawing of the configuration of FIG. 46 in an assembled state.
FIG. 48 is an assembled connector having two opposing ball-receiving sockets.
Figure 50:
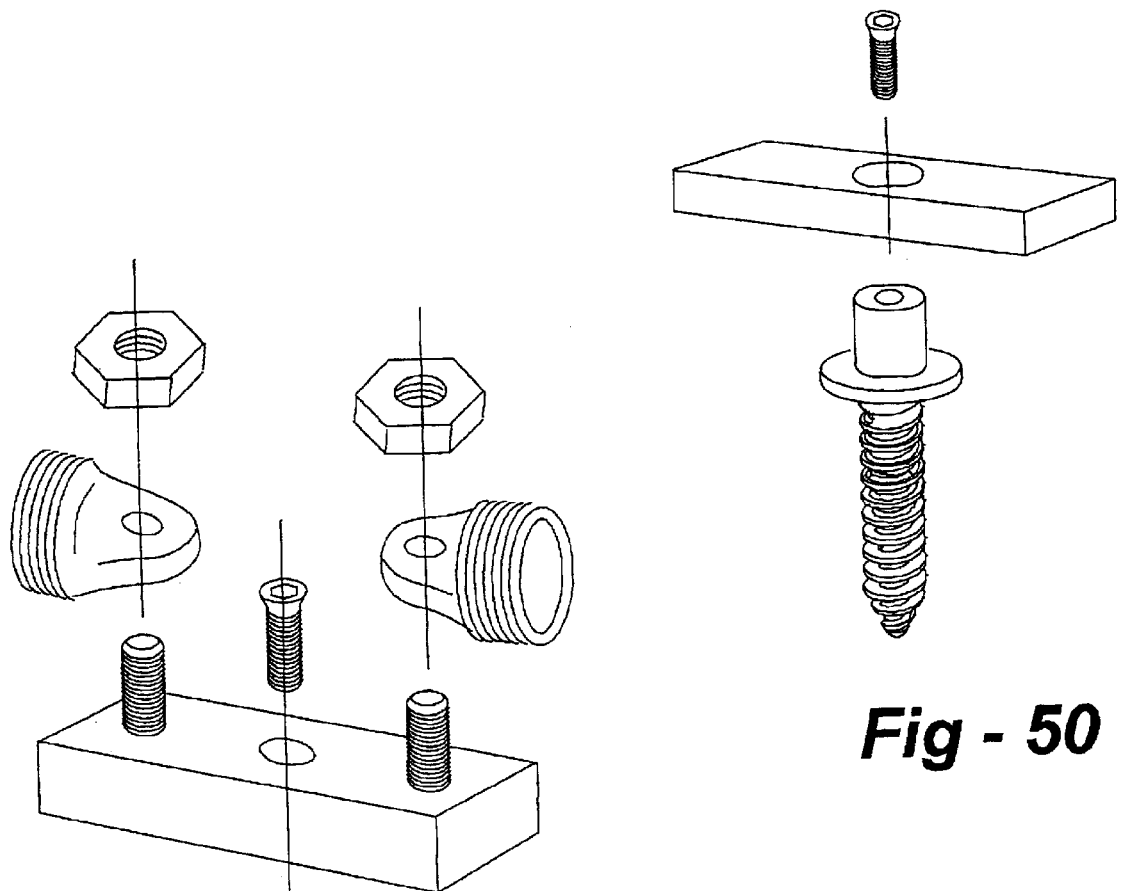
FIG. 50 shows how a non-round (in this case, oval) interconnection may be used to prevent rotation of the pedicle screw relative to a connector body.
Figure 49:
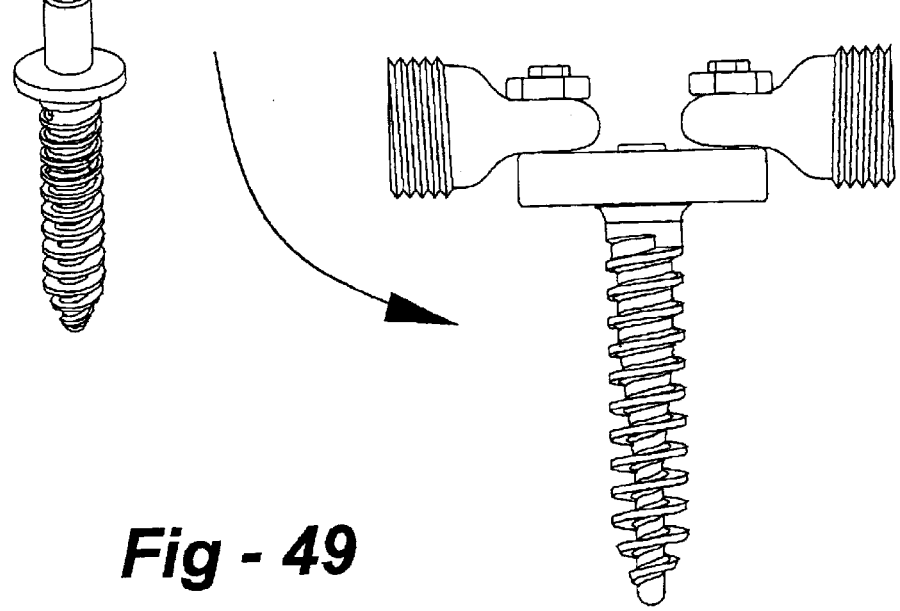
FIG. 49 is a drawing of an exploded and assembled view of a pedicle screw having independent double connectors.

FIG. 46 is a perspective view of the pedicle screw of FIG. 45 including a ball connector and link bar. FIG. 47 is a drawing of the configuration of FIG. 46 in an assembled state. FIG. 48 is an assembled connector having two opposing ball-receiving sockets. Note that pedicle screws for independent double connectors may require a different (i.e., longer) design. FIG. 49 is a drawing of an exploded and assembled view of a pedicle screw having independent double connectors. FIG. 50 shows how a non-round interconnection may be used to prevent rotation of the pedicle screw relative to a connector body.

Figure 51:
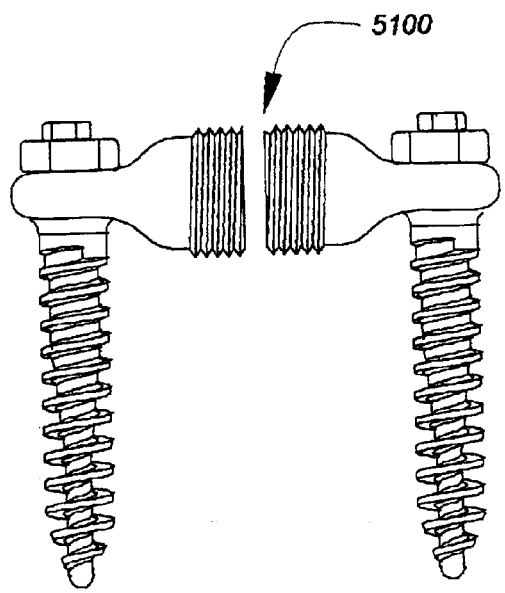
FIG. 51 is a drawing used to introduce the use of a hinged connector according to the invention.
Figure 52A:
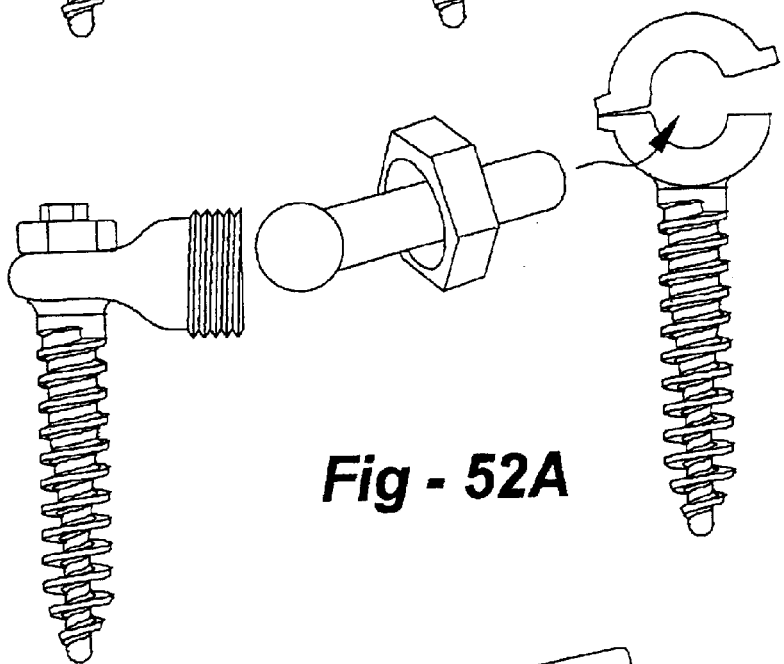
FIG. 52A shows the hinge connector in an open condition.
Figure 52B:
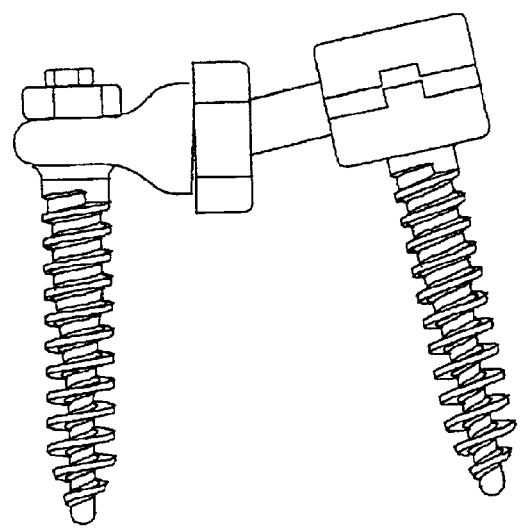
FIG. 52B shows a hinge connector locked onto a rod.

This invention also provides 'open' pedicle screws which may be deployed when there is not enough room at 5100 between screws to allow connectors, as shown in FIG. 51. FIG. 52A shows such a hinged connector in an open condition, whereas FIG. 52B shows the hinged connector locked onto a rod. Indeed, it will be appreciated that most, if not all, of the various embodiments described herein may, at least in some way, be adapted for use with spinal rods of the type now in common use.

Figure 53A:
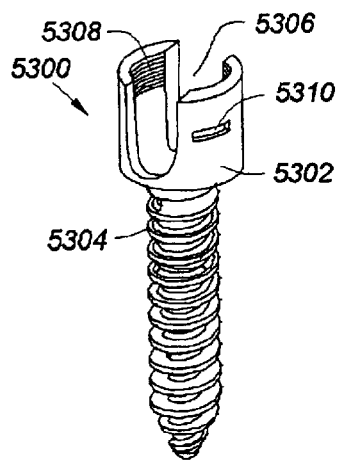
Figure 53B:
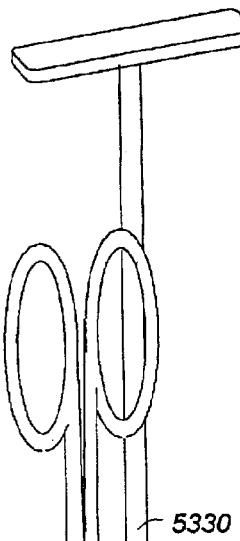
Figure 53C:
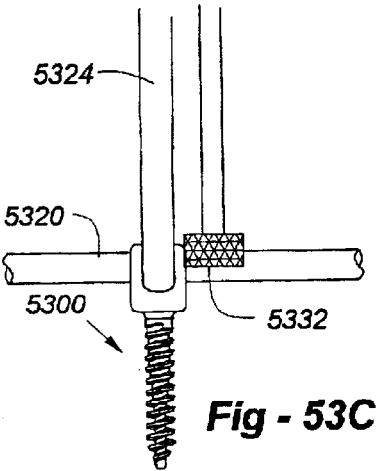

FIGS. 53A–53M illustrate the alternative use of straps according to the invention for rod movement and stabilization. FIG. 53A depicts a pedicle screw 5300 having lower threads 5304 and body 5302 with rod-receiving area 5306 and threads 5308 for a compression fastener (not shown). An indentation 5310 is provided on the side for grasping. Typically, surgeons force spinal rods into such pedicle screws and vertebral hooks with bulky clamps and threaded "rod pushers" as depicted schematically in FIG. 53B. This presents significant disadvantages. For one, the clamps and rod pushers are bulky. The large clamps and pushers also frequently impinge on one another. To avoid impingement, surgeons often place excessive force on a single screw or hook to allow placement of a setscrew to hold to hold the rod in place, enabling the surgeon to remove the clamp. The excessive force on a hook or screw can crack the vertebra, and the bulky clamps may interfere with setscrew placement.

Figure 53E:
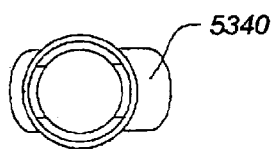
Figure 53F:
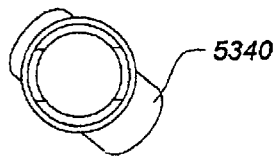
Figure 53D:
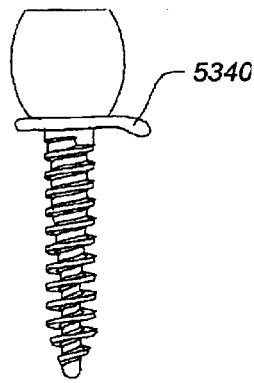

The embodiment of FIGS. 53D through 53M uses wires, cables, or straps to guide spinal rods into pedicle screws and hooks. The preferred embodiment uses plastic straps or cable ties 5344 as tightening tools. FIG. 53D shows the use of a strap piece 5340 for such a purpose. As shown in FIGS. 53E and 53F, the strap piece 5340 is preferably rotatable beneath the body of the rod fastener. As depicted in FIG. 53L, the straps may be removed once the rod is held in place with setscrews or nuts.

FIG. 53G shows a cable tie 5344 engaged with the strap piece 5340 prior to tightening. FIG. 53H shows the cable tie tightened and the rod in place within the pedicle screw. FIG. 53I shows the alternative use of a removable strap piece 5350. FIG. 53J shows a cable tie 5344 engaged with the strap piece 5350 prior to tightening. FIG. 53K shows the cable tie tightened and the rod in place within the pedicle screw. FIG. 53M shows how this and other aspects of the invention are not limited to pedicle screws, but may also be configured for sublaminar hooks and other devices.

The use of cable ties and straps has several advantages. The straps are less bulky than the clamps and pushers currently in use. Straps, with locking mechanisms, hold tension after the tightening tool is removed. As such, the tightening tool can be removed from the wound, giving the surgeon more room to work. Straps can be tightened repeatedly as the rod advances into several hooks or screws. Thus, the loads are shared by multiple spinal attachment sites rather than a single attachment site. Vertebral fracture is therefore less likely. The straps, cables, and wires are lateral to the hook and screw rod connection. Accordingly, the lateral position does not interfere with setscrew placement.

Figure 56:
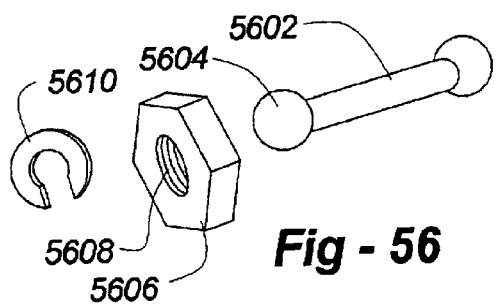
FIG. 56 shows how a half-washer may be used in conjunction with a nut opening that is large enough to slide over the sphere at the end of a rod.
Figure 57:
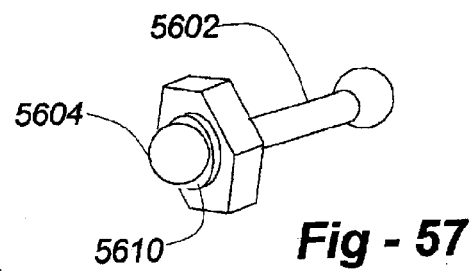
FIG. 57 shows an alternative use of a slotted washer permitting a nut to slide over the spherical end of a solid rod.

The elongated members or rods according to the invention may also be provided in a variety of configurations, including solid-, non-telescoping, telescoping, turnbuckle, and different lengths and shapes. The solid rods with spherical ends may be manufactured with the nuts in position, or half washers may be used as shown in FIGS. 56 and 57 to reduce costs. Rods with single spherical end rods may use nuts added by the surgeon in lengths which may be cut at the time of surgery to customize.

Figure 54:
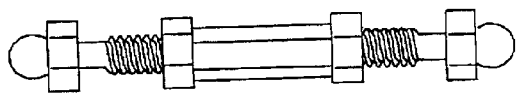
FIG. 54 is a side view of a turnbuckle rod according to the invention.
Figure 55:
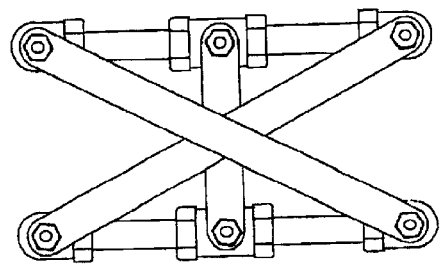
FIG. 55 is a drawing which shows the combined use of ball-and-socket connectors in criss-cross link bars.

FIG. 54 is a side view of a turnbuckle rod according to the invention. Preferably, such a device exhibits a contracted length on the order of 3 cm while being expandable to 10 cm or beyond. Many different sizes may be provided as necessary to accommodate a greater range. FIG. 55 is a drawing which shows the combined use of ball-and-socket connectors in conjunction with optional criss-cross link bars. Such bars are preferably narrow, on the order of 2 mm thick, in 2 cm–10 cm lengths with 3 mm increments.

As discussed above, the nuts may be added to solid rods after the rods are manufactured using half- or slotted washers. FIG. 56 shows how a half-washer 5610 may be used in conjunction with a nut opening 5608 that is large enough to slide over the sphere at the end of a rod. FIG. 57 shows an alternative use of a slotted wash 5610 permitting a nut to slide over the spherical end 5604 of a solid rod 5602.

Figure 58A:
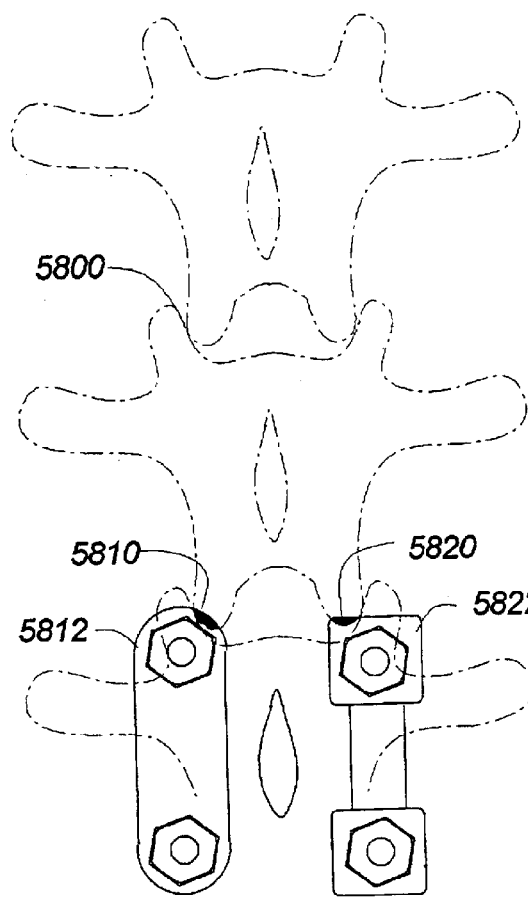
FIG. 58A is a drawing which shows a modified connector adapted may be used to reduce impingement.
Figure 58B:
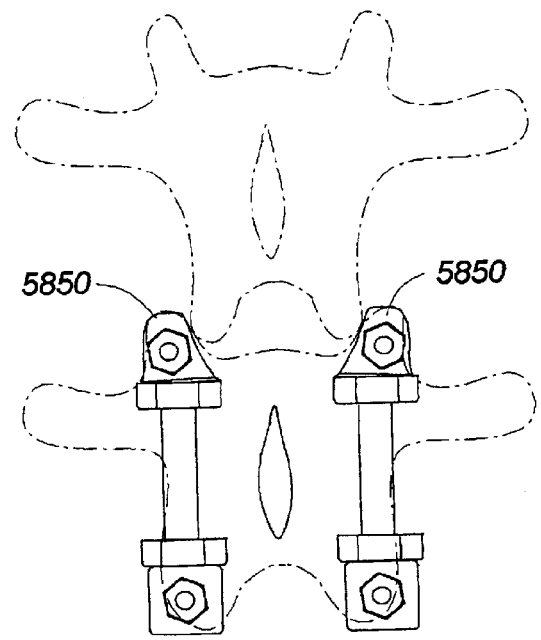
FIG. 58B is a drawing of an anti-impingement connector utilizing a ball-and-socket arrangement.

Prior-art spinal rods, screws, and plates risk impingement on the first mobile facet cephalad to the fusion. For example, the inferior facet of $L_4$ may impinge on the plate, rod, nut, or connector extending from $L_5$ to $S_1$ in a $L_5$–$S_1$ fusion. Impingement can lead to pain, facet arthritis, facet fracture, and additional surgery. What is needed is a reduced profile connector to prevent impingement. FIG. 58A is a drawing which shows a modified connector adapted to reduce impingement. FIG. 58B is a drawing of an anti-impingement connector utilizing a ball-and-socket arrangement.

FIGS. 59A and 59B are different views of a transverse connector according to the invention. The transverse connector (cross brace) fits on the rods between the hooks. FIG. 60 shows the combined use of transverse connectors and hinged hooks which lock onto a solid rod. The convex solid rod may be placed after the modular system to restore the spine to its proper alignment. The convex rod may include an octagonal or other cross-section to prevent rotation of cross brace on the rod, as shown in FIG. 61. For example, the convex rod may have longitudinal grooves. Such features may travel the length of the rod or be interrupted. FIG. 62A illustrates the use of a continuous shaped rod, in this case having a grooved cross-section. FIG. 62B illustrates how the modification along the rod may be interrupted along its length.

FIG. 63 is a drawing which shows a bevel connector embodiment according to the invention. Such a connector allows 15–20 (or more) degrees of angulation before tightening. Although this type of connector is used in current spine implants, prior art configurations use only one rod on each side of spine. This embodiment of the invention allows use of multiple rods/side as shown in FIG. 64. Indeed, it is believed that the modular hooks and screws according to the invention represent the only system that allows two rods to be attached to a single rod hook or screw.

FIG. 65A is a drawing which shows a stabilization clamp for use with various embodiments disclosed herein. FIG. 65B is an end of the configuration of FIG. 65A. FIG. 66A is a different alternative embodiment of a stabilizing assembly, and FIG. 66B is a cross-section of the assembly of FIG. 66A.

FIGS. 67A–67C illustrate the use of lockable swivel-type connectors 6704, 6704', which may be fastened to one or, preferably a pair, of parallel (or non-parallel) rods 6702, 6702' to provide a desired degree of alignment and correction. This particular embodiment uses a modified hook structure and setscrew arrangement, which may be moved along the rod, as shown in FIG. 67B, until a desired degree of separation/ orientation is achieved, at which point all of the various components may be tightened into place with fasteners 6710, 6710'.

To ensure stable interconnections that do not loosen through movement or degrade with time, the invention may take advantage of materials and/or geometries to enhance structural integrity. For example, shape-memory technology may be used to assist in locking the screws, rods, caps, joints and other components to one another. Such interfaces may be mobile until body temperature changes the dimensions to promote a tighter fit, where applicable. In addition, particularly with respect to threaded fastneners, the thread sizes may be slightly mismatched to promote a slight galling for an even tighter fit.

I claim:

1. A spinal alignment system, comprising:
   a rigid elongated element having a first shaped end and a second shaped end, said elongated element dimensioned to span between a first vertebra and a second vertebra;
   a first connecter having a lower portion configured for spinal engagement into said first vertebra, and an upper portion configured to receive said first shaped end of said elongated element such that said elongated element is temporarily angularly movable relative to said first connector;
   a second connecter having a lower portion configured for spinal engagement into said second vertebra, and an upper portion configured to receive said second shaped end of said elongated element;
   a first fastener for locking said first shaped end of said elongated element into position relative to said first connector once a desired angular relationship is established between said elongated element and said first connecter; and
   a second fastener for locking said second shaped end of said elongated element into position relative to said second connector.

2. The spinal alignment system of claim 1, wherein said lower portion of at least one of said first connector and said second connector comprises a pedicle screw.

3. The spinal alignment system of claim 1, wherein said lower portion of at least one of said first connector and said second connector comprises a subliminar hook.

4. The spinal alignment system of claim 1, wherein at least one of said first and second fasteners comprise a threaded compression fastener.

5. The spinal alignment system of claim 1, including a first tension band configured to be positioned around the upper portion of said first connector, and a second tension band configured to be positioned around said upper portion of said second connector.

6. The spinal alignment system of claim 1, further including a strap engagement feature associated with at least one of said first and second connectors, enabling a cable tie to be placed around said engagement feature and said elongated element such that said cable tie may be tightened to thereby pull said elongated element into engagement with said upper portion.

7. The spinal alignment system of claim 1, wherein said upper portion and said lower portion of at least one of said first and second connectors are formed as a unitary article such that said upper and lower portions are fixed relative to one another.

8. The spinal alignment system of claim 1, wherein said upper portion and said lower portion of at least one of said first and second connectors are formed as separate articles coupled together such that said upper and lower portions are angularly movable relative to one another prior to being locked in position by at least one of said first and second fasteners.

9. The spinal alignment system of claim 1, wherein said elongated element includes a rod portion extending between said first and second shaped ends, said rod portion having cross section which is at least one of a circle, a regular polygon, and a hexagon.

10. The spinal alignment system of claim 1, wherein said first and second vertebrae are at adjacent vertebral levels within the spine.

11. The spinal alignment system of claim 1, wherein said first and second vertebrae are not at adjacent vertebral levels within the spine.

12. The spinal alignment system of claim 1, wherein at least one of said first and second shaped ends of said elongate element comprises an at least partially spherical end, and wherein said respective upper portion includes a partially spherical receiving area to receive said at least partially spherical end, and at least one side opening through which said elongated element extends.

13. The spinal alignment system of claim 12, further including half spherical caps coupled to said at least partially spherical ends of said elongated element, thereby forming ball-shaped ends to be received within said upper portions of said first and second connectors body.

14. The spinal alignment system of claim 1, wherein said shaped end of said elongated element has a generally circular cross section.

15. The spinal alignment system of claim 14, wherein said 1001 shaped ends comprises flat disks capable of being stacked onto one another such that multiple elongated elements may be coupled to and extend from at least one of the first and second connectors.

16. The spinal alignment system of claim 1, wherein said elongated element further includes a length-adjustment mechanism.

17. The spinal alignment system of claim 16, wherein said length-adjustment mechanism is telescoping.

18. The spinal alignment system of claim 16, wherein said length-adjustment mechanism includes a turnbuckle.

19. The spinal alignment system of claim 1, wherein said elongated element includes a first sub-element and a second sub-element, each having ends that terminate in half spheres such that said half spheres may, be mated to form a single spherical joint.

20. The spinal alignment system of claim 19, further including a feature to maintain the spherical shape of said joint as said first and second sub-elements are angled relative to one another.

21. The spinal alignment system of claim 19, wherein said half spherical ends of said first and second sub-elements each include a flat surface such that said first and second sub-elements mate by positioning said flat surface of said first sub-element against said flat surface of said second sub-element.

22. The spinal alignment system of claim 21, wherein each of said first and second sub-elements defines an axis, and said flat surface is not perpendicular to said axis.

23. The spinal alignment system of claim 19, wherein said single spherical joint may be coupled a third connector having a lower portion configured for spinal engagement into a third vertebra disposed between said first and second vertebra, and an upper portion configured to receive said single spherical joint of said elongate element, wherein said upper portion has opposing side openings through which said first sub-element and said second sub-element extend.

24. The spinal alignment system of claim 23, wherein said first sub-element and said second sub-element may be angled relative to one another while maintaining said single spherical joint, such that a third fastener may be used to lock said single spherical joint into position to achieve a desired angular relationship between each of said first and second sub-elements and said third connector.

25. The spinal alignment system of claim 23, wherein said third vertebra and at least one of said first and second vertebrae are at adjacent vertebral levels within the spine.

26. A spinal alignment system, comprising:
a rigid elongated element having a first shaped end and a rod portion, said elongated element dimensioned to span between a first vertebra and a second vertebra;
a first bone engagement member configured for spinal engagement into said first vertebra, said first bone engagement member having an first upper body portion dimensioned to receive said first shaped end of said elongated element such that said elongated element is temporarily angularly movable relative to said first upper body portion;
a second bone engagement member configured for spinal engagement into said second vertebra, said second bone engagement member having an second upper body portion dimensioned to receive said rod portion of said elongated element;
a first fastener for locking said first shaped end of said elongated element within said first upper body portion once a desired angular relationship is established therebetween; and
a second fastener for locking said rod portion of said elongated element within said second upper body portion.

27. The spinal alignment system of claim 26 and further, wherein said first bone engagement member and said first upper body portion are separate articles coupled together to be angularly moveable with respect to one another prior to being locked by said first fastener.

28. The spinal alignment system of claim 26 and further, wherein said second bone engagement member and said second upper body portion are separate articles coupled together to be angularly moveable with respect to one another prior to being locked by said second fastener.

29. The spinal alignment system of claim 26, and further, wherein said first bone engagement member and said first upper body portion comprise a unitary article such that said first bone engagement member and said first upper body portion are not angularly moveable with respect to one another.

30. The spinal alignment system of claim 26, and further, wherein said second bone engagement member and said second upper body portion comprise a unitary article such that said second bone engagement member and said second upper body portion are not angularly moveable with respect to one another.

31. The spinal alignment system of claim 26 and further, wherein said rod portion of said elongated element has a cross section which is at least one of a circle, a regular polygon, and a hexagon.

32. The spinal alignment system of claim 26 and further, wherein said first shaped end has a generally circular cross section.

33. The spinal alignment system of claim 26 and further, wherein said first shaped end comprises at least a partial spherical shape.

34. The spinal alignment system of claim 26 and further, wherein said first shaped end comprises a flat disk.

35. The spinal alignment system of claim 26 and further, wherein said first upper body portion is also configured to receive said rod portion of said elongated element.

36. The spinal alignment system of claim 26 and further, wherein said second upper body portion is also configured to receive said first shaped end of said elongated element.

37. The spinal alignment system of claim 26, wherein said first and second vertebrae are at adjacent vertebral levels within the spine.

38. The spinal alignment system of claim 26, and further, wherein said first and second vertebrae are not at adjacent vertebral levels within the spine.

39. The spinal alignment system of claim 26 and further, wherein said at least one of said first and second bone engagement members comprises a pedicle screw.

40. The spinal alignment system of claim 26 and further, wherein said at least one of said first and second bone engagement members comprises a sublaminar hook.

41. The spinal alignment system of claim 26 and further, wherein said elongated element includes a second shaped end opposite said first shaped end.

42. The spinal alignment system of claim 41 and further, wherein said second shaped end is dimensioned to be received within said second upper body portion.

43. The spinal alignment system of claim 26 and further, wherein said elongated element comprises a first sub-element having a first engagement surface, and a second sub-element having a second engagement surface, said first and second engagement surfaces mating to form a single spherical joint.

44. The spinal alignment system of claim 43 and further, comprising a third bone engagement member configured for spinal engagement into a third vertebra located between said first and second vertebrae, and including an upper body portion dimensioned to receive said single spherical joint formed by the mating of said first and second sub-elements of said elongated element.

45. The spinal alignment system of claim 43, wherein said first and second engagement surfaces are flat.

46. The spinal alignment system of claim 43, wherein said first and second flat engagement surfaces are angled relative to the longitudinal axis of the first and second sub-elements, respectively, such that the first and second sub-elements may be angled relative to one another while maintaining said single spherical joint.

47. A spinal alignment system, comprising:
a rigid elongated element having a first shaped end, a second shaped end, and a rod portion, said elongated element dimensioned to span between a first vertebra and a second vertebra;
a first bone engagement member configured for spinal engagement into said first vertebra, said first bone engagement member having an first upper body portion dimensioned to receive said first shaped end of said elongated element such that said elongated element is temporarily angularly movable relative to said first upper body portion;

a second bone engagement member configured for spinal engagement into said second vertebra, said second bone engagement member having an second upper body portion dimensioned to receive at least one of said rod portion and said second shaped end of said elongated element;

a first fastener for locking said first shaped end of said elongated element within said first upper body portion once a desired angular relationship is establish therebetween; and a second fastener for locking at least one of said rod portion and said second shaped end of said elongated element within said second upper body portion.

48. The spinal alignment system of claim 47 and further, wherein said first bone engagement member and said first upper body portion are separate articles coupled together to be angularly moveable with respect to one another prior to being locked by said first fastener.

49. The spinal alignment system of claim 47 and further, wherein said second bone engagement member and said second upper body portion are separate articles coupled together to be angularly moveable with respect to one another prior to being locked by said second fastener.

50. The spinal alignment system of claim 47 and further, wherein said first bone engagement member and said first upper body portion comprise a unitary article such that said first bone engagement member and said first upper body portion are not angularly moveable with respect to one another.

51. The spinal alignment system of claim 47 and further, wherein said second bone engagement member and said second upper body portion comprise a unitary article such that said second bone engagement member and said second upper body portion are not angularly moveable with respect to one another.

52. The spinal alignment system of claim 47 and further, wherein said rod portion of said elongated element has a cross section which is at least on of a circle, a regular polygon, and a hexagon.

53. The spinal alignment system of claim 47, and further, wherein at least one of said first and second shaped end has a generally circular cross section.

54. The spinal alignment system of claim 47, and further, wherein at least one of said first and second shaped end comprises at least a partial spherical shape.

55. The spinal alignment system of claim 47, and further, wherein at least one of said first and second shaped end comprises a flat disk.

56. The spinal alignment system of claim 47, and further, wherein said first upper body portion is also configured to receive said rod portion of said elongated element.

57. The spinal alignment system of claim 47, wherein said first and second vertebrae are at adjacent vertebral levels within the spine.

58. The spinal alignment system of claim 47 and further, wherein said first and second vertebrae are not at adjacent vertebral levels within the spine.

59. The spinal alignment system of claim 47 and further, wherein said at least one of said first and second bone engagement members comprises a pedicle screw.

60. The spinal alignment system of claim 47 and further, wherein said at least one of said first and second bone engagement members comprises a sublaminar hook.

61. The spinal alignment system of claim 47 and further, wherein said elongated element comprises a first element having a first engagement surface, and a second element having a second engagement surface, said first and second engagement surfaces mating to form a single spherical joint.

62. The spinal alignment system of claim 61 and further, comprising a third bone engagement member configured for spinal engagement into a third vertebra located between said first and second vertebrae, and including an upper body portion dimensioned to receive said single spherical joint formed by the mating of said first and second elements of said elongated element.

63. The spinal alignment system of claim 61, wherein said first and second engagement surfaces are flat.

64. The spinal alignment system of claim 61, wherein said first and second flat engagement surfaces are angled relative to the longitudinal axis of the first and second elements, respectively, such that the first and second elements may be angled relative to one another while maintaining said single spherical joint.

* * * * *